(12) United States Patent
Horseman et al.

(10) Patent No.: US 9,889,311 B2
(45) Date of Patent: Feb. 13, 2018

(54) SYSTEMS, PROTECTIVE CASINGS FOR SMARTPHONES, AND ASSOCIATED METHODS TO ENHANCE USE OF AN AUTOMATED EXTERNAL DEFIBRILLATOR (AED) DEVICE

(71) Applicant: Saudi Arabian Oil Company, Dhahran (SA)

(72) Inventors: Samantha J. Horseman, Dhahran (SA); Curtis Gonter, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 225 days.

(21) Appl. No.: 14/959,250

(22) Filed: Dec. 4, 2015

(65) Prior Publication Data

US 2017/0157415 A1 Jun. 8, 2017

(51) Int. Cl.
*A61N 1/39* (2006.01)
*A61N 1/362* (2006.01)
(Continued)

(52) U.S. Cl.
CPC ......... *A61N 1/3968* (2013.01); *A61N 1/0492* (2013.01); *A61N 1/3625* (2013.01);
(Continued)

(58) Field of Classification Search
CPC .. A61N 1/3975; A61N 1/3925; A61N 1/3625; A61N 1/3968; A61N 1/3993; A61N 1/3987; A61N 1/0492; A61N 1/046
See application file for complete search history.

(56) References Cited

U.S. PATENT DOCUMENTS

| 4,951,963 A | 8/1990 | Behr et al. |
| 4,998,534 A | 3/1991 | Claxton, III et al. |

(Continued)

FOREIGN PATENT DOCUMENTS

| AU | 767533 B2 | 11/2003 |
| CN | 101065752 A | 10/2007 |

(Continued)

OTHER PUBLICATIONS

Duke, Sean, "A 'smartphone' based defibrillator" Science Spin, Jan. 11, 2011; pp. 1-2.
(Continued)

*Primary Examiner* — Alyssa M Alter
(74) *Attorney, Agent, or Firm* — Bracewell LLP; Constance G. Rhebergen; Christopher L. Drymalla

(57) ABSTRACT

Embodiments of the invention include systems, protective casings for smartphones, and associated methods to enhance use of an automated external defibrillator (AED) device before arrival of emergency medical personnel. A system can include a smartphone and a protective casing abuttingly contacting one or more side portions of the smartphone and retaining the smartphone positioned therein. The smartphone can include a defibrillation control module to control defibrillation of a victim of sudden cardiac arrest. The protective casing can include sensors, capacitors, and extendable electrode pads. The protective casing further can include a check module to determine whether the victim's heart rhythm requires an electrical shock to reestablish a normal heart rhythm, a space module to measure presence and amount of preselected materials relatively near the system, and a shock module to activate the one or more capacitors and generate an electrical current to deliver an electrical shock to the victim's chest.

22 Claims, 25 Drawing Sheets

(51) Int. Cl.
  *H04W 88/02*    (2009.01)
  *H04B 1/3888*   (2015.01)
  *H04M 1/04*     (2006.01)
  *H04M 1/21*     (2006.01)
  *H04W 4/22*     (2009.01)
  *A61N 1/04*     (2006.01)
  *A45C 11/00*    (2006.01)

(52) U.S. Cl.
  CPC ....... *A61N 1/3925* (2013.01); *A61N 1/39044* (2017.08); *A61N 1/3975* (2013.01); *A61N 1/3987* (2013.01); *A61N 1/3993* (2013.01); *H04B 1/3888* (2013.01); *H04M 1/04* (2013.01); *H04M 1/21* (2013.01); *H04W 4/22* (2013.01); *H04W 88/02* (2013.01); *A45C 2011/002* (2013.01); *A61N 1/046* (2013.01)

(56) References Cited

U.S. PATENT DOCUMENTS

| | | |
|---|---|---|
| 5,000,188 A | 3/1991 | Kojima |
| 5,111,539 A | 5/1992 | Hiruta et al. |
| 5,253,656 A | 10/1993 | Rincoe et al. |
| 5,304,112 A | 4/1994 | Mrklas et al. |
| 5,305,238 A | 4/1994 | Starr, III |
| 5,323,650 A | 6/1994 | Fullen et al. |
| 5,331,549 A | 7/1994 | Crawford, Jr. |
| 5,343,869 A | 9/1994 | Pross et al. |
| 5,410,471 A | 4/1995 | Alyfuku et al. |
| 5,435,315 A | 7/1995 | McPhee et al. |
| 5,441,047 A | 8/1995 | David |
| 5,542,420 A | 8/1996 | Goldman et al. |
| 5,570,301 A | 10/1996 | Barrus |
| 5,573,269 A | 11/1996 | Gentry et al. |
| 5,626,145 A | 5/1997 | Clapp et al. |
| 5,673,691 A | 10/1997 | Abrams et al. |
| 5,792,047 A | 8/1998 | Coggins |
| 5,813,993 A | 9/1998 | Kaplan |
| 5,937,387 A | 8/1999 | Summerell et al. |
| 6,033,344 A | 3/2000 | Trulaske et al. |
| 6,049,281 A | 4/2000 | Osterweil |
| 6,080,106 A | 6/2000 | Lloyd et al. |
| 6,083,156 A | 7/2000 | Lisiecki |
| 6,104,296 A | 8/2000 | Yasuchi et al. |
| 6,148,280 A | 11/2000 | Kramer |
| 6,149,586 A | 11/2000 | Elkind |
| 6,190,314 B1 | 2/2001 | Ark et al. |
| 6,198,394 B1 | 3/2001 | Jacobsen et al. |
| 6,203,495 B1 | 3/2001 | Bardy |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,345,839 B1 | 2/2002 | Kuboki et al. |
| 6,353,764 B1 | 3/2002 | Imagawa et al. |
| 6,369,337 B1 | 4/2002 | Machiyama |
| 6,381,577 B1 | 4/2002 | Brown |
| 6,383,136 B1 | 5/2002 | Jordan |
| 6,408,263 B1 | 6/2002 | Summers |
| 6,425,862 B1 | 7/2002 | Brown |
| 6,450,530 B1 | 9/2002 | Frasher et al. |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,594,607 B2 | 7/2003 | Lavery |
| 6,646,556 B1 | 11/2003 | Smith |
| 6,648,820 B1 | 11/2003 | Sarel |
| 6,658,572 B1 | 12/2003 | Craig |
| 6,669,286 B2 | 12/2003 | Iusim |
| 6,673,027 B2 | 1/2004 | Fischer |
| 6,675,130 B2 | 1/2004 | Kanevsky et al. |
| 6,692,258 B1 | 2/2004 | Kurzweil |
| 6,705,990 B1 | 3/2004 | Gallant et al. |
| 6,736,642 B2 | 5/2004 | Bajer |
| 6,767,330 B2 | 7/2004 | Lavery et al. |
| 6,768,246 B2 | 7/2004 | Pelrine et al. |
| 6,781,067 B2 | 8/2004 | Montagnino et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,931,359 B2 | 8/2005 | Tamada |
| 6,982,497 B2 | 1/2006 | Rome |
| 7,005,757 B2 | 2/2006 | Pandian |
| 7,027,621 B1 | 4/2006 | Prokoski |
| 7,074,198 B2 | 7/2006 | Krullaards |
| 7,104,965 B1 | 9/2006 | Jiang et al. |
| 7,109,872 B2 | 9/2006 | Balaban et al. |
| 7,128,577 B2 | 10/2006 | Renaud |
| 7,152,024 B2 | 12/2006 | Marschner |
| 7,155,158 B1 | 12/2006 | Iuppa |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallenberger |
| 7,304,580 B2 | 12/2007 | Sullivan et al. |
| 7,315,249 B2 | 1/2008 | Littell |
| 7,351,206 B2 | 4/2008 | Suzuki |
| 7,399,276 B1 | 7/2008 | Brown et al. |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,717,866 B2 | 5/2010 | Damen |
| 7,771,318 B2 | 8/2010 | Narayanaswami |
| 7,830,249 B2 | 11/2010 | Dorneich et al. |
| 7,844,347 B2 | 11/2010 | Brabec et al. |
| 7,849,115 B2 | 12/2010 | Reiner |
| 7,901,324 B2 | 3/2011 | Kodama |
| 7,958,002 B2 | 6/2011 | Bost |
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,180,457 B2 | 5/2012 | Matos |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,359,231 B2 | 1/2013 | Fitzpatrick et al. |
| 8,428,962 B1 | 4/2013 | Brinkley et al. |
| 8,477,039 B2 | 7/2013 | Gleckler et al. |
| 8,487,456 B2 | 7/2013 | Donelan et al. |
| 8,597,121 B2 | 12/2013 | Andres Del Valle |
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer et al. |
| 8,775,196 B2 | 7/2014 | Simpson et al. |
| 8,956,292 B2 | 2/2015 | Wekell et al. |
| 9,043,217 B2 | 5/2015 | Cashman et al. |
| 9,044,172 B2 | 6/2015 | Baxi et al. |
| 9,364,714 B2 | 6/2016 | Koduri et al. |
| 2001/0039372 A1 | 11/2001 | Yasushi et al. |
| 2001/0040591 A1 | 11/2001 | Abbott et al. |
| 2001/0041845 A1 | 11/2001 | Kim |

(56) References Cited

U.S. PATENT DOCUMENTS

| | | |
|---|---|---|
| 2001/0042004 A1 | 11/2001 | Taub |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0222440 A1 | 12/2003 | Basir |
| 2003/0226695 A1 | 12/2003 | Mault |
| 2004/0002634 A1 | 1/2004 | Nihtila |
| 2004/0015191 A1 | 1/2004 | Otman et al. |
| 2004/0095378 A1 | 5/2004 | Vigue |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Iran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0015422 A1 | 6/2008 | Wessel |
| 2008/0140140 A1 | 6/2008 | Grimley et al. |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Duwekerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |

(56) References Cited

U.S. PATENT DOCUMENTS

| | | |
|---|---|---|
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Guoyi et al. |
| 2010/0312606 A1 | 12/2010 | Gala |
| 2010/0332250 A1 | 12/2010 | Simpson |
| 2011/0033830 A1 | 2/2011 | Cherian |
| 2011/0035231 A1 | 2/2011 | Firminger et al. |
| 2011/0046688 A1 | 2/2011 | Schwibner et al. |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Hotary et al. |
| 2012/0117020 A1 | 5/2012 | Davis et al. |
| 2012/0122430 A1 | 5/2012 | Hutchings et al. |
| 2012/0127157 A1 | 5/2012 | Adler |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0226413 A1 | 8/2013 | Cuddihy et al. |
| 2013/0234826 A1 | 9/2013 | Sekiguchi et al. |
| 2013/0243208 A1 | 9/2013 | Fawer |
| 2013/0281798 A1 | 10/2013 | Rau et al. |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2013/0308099 A1 | 11/2013 | Stack |
| 2013/0331993 A1 | 12/2013 | Detsch et al. |
| 2013/0334851 A1 | 12/2013 | Hoell et al. |
| 2014/0067001 A1 | 3/2014 | Schwibner et al. |
| 2014/0100464 A1 | 4/2014 | Kaleal et al. |
| 2014/0107718 A1 | 4/2014 | Foote et al. |
| 2014/0129401 A1 | 5/2014 | Kruz et al. |
| 2014/0156259 A1 | 6/2014 | Dolan et al. |
| 2014/0172461 A1 | 6/2014 | Rogers |
| 2014/0222095 A1 | 8/2014 | Einy |
| 2014/0222096 A1 | 8/2014 | Hu et al. |
| 2014/0317914 A1 | 10/2014 | Shaker |
| 2015/0025928 A1 | 1/2015 | Kang et al. |
| 2015/0199494 A1 | 7/2015 | Koduri et al. |
| 2015/0222096 A1 | 8/2015 | Nakayama |
| 2015/0338265 A1 | 11/2015 | Carreel et al. |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |
| EP | 1407713 B1 | 9/2008 |
| EP | 2151355 A1 | 2/2010 |
| EP | 2248461 A2 | 11/2010 |
| EP | 2924674 A1 | 9/2015 |
| JP | 05-049603 A | 3/1993 |
| JP | H07204168 A | 8/1995 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001356849 A | 12/2001 |
| JP | 2002109061 A | 4/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003235813 A | 8/2003 |
| JP | 2003247991 A | 9/2003 |
| JP | 2003256578 A | 9/2003 |

(56) References Cited

FOREIGN PATENT DOCUMENTS

| | | |
|---|---|---|
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 2001028416 A1 | 4/2001 |
| WO | 2001086403 A2 | 11/2001 |
| WO | 03077110 A2 | 9/2003 |
| WO | 2005064447 A2 | 7/2005 |
| WO | 2006022465 A2 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | 2014023422 | 2/2014 |

OTHER PUBLICATIONS

Sasson, Comilla, et al.; "Predictors fo Survival From Out-Of Hospital Cardiac Arrest: A systematic Review and Meta-Analysis" Circ Cardiovasc Qual Outcomes Jan. 2010; DOI: 10.1161/CIRCOUTCOMES.109.889576; pp. 63-81.
Hallstrom, Alfred and Ornato, Joseph P.; "Public-Access Defibrilation and Survival after Out-of-Hospital Cardiac Arrest" The New England Journal of Medicine vol. 351, No. 7, Aug. 12, 2004; pp. 637-646.
Eftestol, Trygve, et al.; "Effects of Cardiopulmonary Resuscitation on Predictors of Ventricular Fibrillation Defibrillation Success During Out-of-Hospital Cardiac Arrest" Circulation Jul. 6, 2004, DOI: 10.1161/01.CIR.0000133323.155653.75; pp. 10-15.
Bobrow, Bentley J., et al.; "Chest Compression-Only CPR by Lay Rescuers and Survival From Out-of-Hospital Cardiac Arrest" JAMA, Oct. 6, 2010—vol. 304, No. 13; pp. 1447-1454.
Nichol, Graham, et al.; "Regional Variation in Out-of-Hospital Cardiac Arrest Incidence and Outcome" JAMA Sep. 24, 2008, vol. 300, No. 12; pp. 1-13.
Weisfeldt, Myron L., et al.; "Survival After Application of Automatic External Defibrillators Before Arrival of the Emergency Medical System" Journal of the American College of Cardiology, vol. 55, No. 16, 2010; pp. 1713-1720.
Sasson, Comilla, et al.; "Association of Neighborhood Characteristics with Bystander-Initiated CPR" The New England Journal of Medicine, Oct. 25, 2012; pp. 1607-1615.
Moon, Sungwoo, et al.; "Abstract 283: Disparities in Bystander CPR and Neurologic Outcomes From Cardiac Arrest According to Neighborhood Ethnicity Characteristics in Arizona" circ.ahajournals.org Circulation. 2013; 128:A283; pp. 1-2.
Moon, Sungwoo, et al.; Abstract 103: Analysis of Out-of-Hospital Cardiac Arrest Location and Public Access Defibrillator Placement in Metro Phoenix, Arizona circ.ahajournals.org Circulation. 2013; 128:A103; pp. 1-2.
Zipes, Douglas P.; "TASER Electronic Control Devices Can Cause Cardiac Arrest in Humans" Circulation Jan. 7, 2014; DOI: 10.1161/CIRCULATIONAHA.113.005504; pp. 101-111.
Abella, Benjamin S., et al.; "Untrained Volunteers Perform High Quality CPR When Using and Automatic External Defibrillator with a CPR Voice Prompting Algorithm" Supplement to Circulation, vol. 116, No. 16, Oct. 16, 2007; pp. 1-2.
DAIS Analytic webpage, available at www.daisanalytic.com as of Jun. 16, 2016; pp. 1-26.
mPhase Technologies webpage, available at www.mphasetech.com as of Jun. 16, 2016; pp. 1-17.
AZoNano "Fuel Cells—Potential Application in Space and Nanotechnology for Improving Fuel Cells" Mar. 2, 2005; pp. 1-3.
"Nanotechnology applications for energy sector" available at http://www.wifinotes.com/nanotechnology/energy-applications-of-nanotechnology.html as of Jun. 16, 2016; pp. 1-3.
Knikou, Maria; "The H-reflex as a probe: Pathways and pitfalls" Journal of Neuroscience Methods 171 (2008); pp. 1-12.
Agarabit Mina, et al., "A sEMG-based Method for Assessing the Design of Computer Mice" 26th Annual International Conference of the IEEE EMBS, Sep. 1-5, 2004; pp. 2450-2453.
Robertini, Nadia, et al., "Capture of Arm-Muscle Deformations using a Depth-Camera" 10 European Conference on Visual Media Production, London, UK, Nov. 6-7, 2013; pp. 1-10.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Hacker, et al. "Representation and visualization of variability in a 3D anatomical atlas using the kidney as an example." Medical Imaging. International Society for Optics and Photonics, 2006. XP055342027 (pp. 1-7).
International Search Report and Written Opinion for International Application No. PCT/US2016/064518; International Filing Date Dec. 2, 2016; Report dated Feb. 17, 2017; (pp. 1-16).
International Search Report and Written Opinion for International Application No. PCT/US2016/065042; International Filing Date Dec. 6, 2016; Report dated Mar. 17, 2017; pp. 1-15.
International Search Report and Written Opinion for International PCT application PCT/US2016/064520; International Filing Date Dec. 2, 2016; Report dated Mar. 27, 2017; pp. 1-10.
International Search Report and Written Opinion for International PCT application PCT/US2016/064521; International Filing Date Dec. 2, 2016; Report dated Mar. 20, 2017; pp. 1-17.
Stephens: "I am 38. My heart is only 33, but my lungs are aged 52. Why?" Mail Online; http://www.dailymail.co.uk/health/article-1249009/I-38-My-heart-only33-lungs-aged-52-Why.html; retrieved on Feb. 3, 2017; XP055342045 (pp. 1-7).
Brown et al, "Prowess Proactive Wellness Environment Support System", Dec. 10, 2009, pp. 1-19, www.hsi.gatech.edu/onsitecenter/index.php/PROWESS.
Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.
Campbell et al., "The Rise of People-Centric Sensing", IEEE Computer Society, 2008, pp. 12-21, IEEE.
Chapman, L., "Expert opinions on 'best practice' in worksite health promotion (WHP)", Jul./Aug. 2004, pp. 1-13.
Chapman, L.. "Meta-evaluation of worksite health promotion economic return studies: 2012 Update", Mar./Apr. 2012, pp. 1-13.
Chapman, Larry S. MPH, "Meta-evaluation of Worksite Health Promotion Economic Return Studies: 2005 Update", Jul./Aug. 2005. (pp. 1-11).
Collins English Dictionary, definition of mat, 2008, retrieved at www.collinsdictionary.com.
Duke, Sean, "A 'smartphone' based defibrillator" Science Spin, Jan. 11, 2011: pp. 1-2.

(56) References Cited

OTHER PUBLICATIONS

Dux, Paul E., and René Marois. "The attentional blink: A review of data and theory." Attention, Perception, & Psychophysics 71.8 (2009): 1683-1700.
Dux, Paul E., et al. "Training improves multitasking performance by increasing the speed of information processing in human prefrontal cortex." Neuron 63.1 (2009): 127-138.
Edington, D. W., "Emerging research: a view from one research centre", American Journal of Health Promotion, 15(5), May/Jun. 2001, pp. 341-349.
Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.
Electric double-layer capacitor Wikipedia; available at the website: http://en.wikipedia.org/wiki/electric_double-layer_capacitor as of Dec. 5, 2014; pp. 1-8.
Elliott, Stephen N., et al. "Cognitive load theory: Instruction-based research with applications for designing tests." Proceedings of the National Association of School Psychologists' Annual Convention, Boston, MA, February. vol. 24. 2009.
EPO: "Notice from the European Patent Office dated Oct. 1, 2007 concerning business methods" Official Journal EPO, vol. 30, No. 11, Nov. 1, 2007, pp. 592-593, XP007905525.
Fadel, Charles, et al. "Multimodal Learning Through Media: What the Research Says" Cisco Systems, Inc. (2008) pp. 1-24.
Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.
Filmer, Hannah L., et al. "Disrupting prefrontal cortex prevents performance gains from sensory-motor training." The Journal of Neuroscience 33.47 (2013): 18654-18660.
Fougnie, Daryl, and René Marois. "What limits working memory capacity? Evidence for modality-specific sources to be simultaneous storage of visual and auditory arrays." Journal of Experimental Psychology: Learning, Memory, and Cognition 37.6 (2011): 132.
Georgia Tech, "Prowess Proactive Wellness Environment Support System", Dec. 12, 2009, pp. 1-27, www.hsi.gatech.edu/onsitecenter/index.php/PROWESS.
Goetzel et al. "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.
Goetzel et al. 'Estimating the Return-on-Investment From Changes in Employee Health Risks on TheDow Chemical Company's Health Care Costs'—J Occup Environ Med. (JOEM) vol. 47, No. 8, dated Aug. 2005; pp. 759-768.
Goetzel et al. 'Health, Absence, Disability, and Presenteeism Cost Estimates of Certain Physical and MentalHealth Conditions Affecting U.S. Employers'—J Occup Environ Med. (JOEM) vol. 46, No. 4, dated Apr. 2004; pp. 398-412.
Goetzel et al. 'Second-Year Results of an Obesity Prevention Program at TheDow Chemical Company'—J Occup Environ Med. (JOEM) vol. 52, No. 3, dated Mar. 2010; pp. 291-302.
Goetzel et al. 'The Health and Productivity Cost Burden of the "Top 10" Physical and Mental HealthConditions Affecting Six Large U.S. Employers in 1999'—J Occup Environ Med. (JOEM) vol. 45, No. 1, dated Jan. 2003; pp. 5-14.
Goetzel et al. 'The Long-Term Impact of Johnson & Johnson's Health & Wellness Program onEmployee Health Risks'—J Occup Environ Med. (JOEM) vol. 44, No. 5, dated May 2002; pp. 417-424.
Goetzel et al. 'The Workforce Wellness Index'—J Occup Environ Med. (JOEM) vol. 55, No. 3, dated Mar. 2013; pp. 272-279.
Goetzel et al. The Predictive Validity of the HERO Scorecard in Determining Future Health Care Cost and Risk Trends—J Occup Environ Med. (JOEM) vol. 56, No. 2, dated Feb. 2014; pp. 136-144.
Health/Medical Writers eHealthcareWorld 2000. (May 1). MyDailyHealth.com (pp. 1-3).
Hemp, P., "Presenteeism: At Work—But Out of It", Harvard Business Review, Oct. 2004, pp. 49-58.
Hill, Jr., Randall W.; "How Virtual Humans Can Build Better Leaders" Harvard Business Review Jul. 25, 2014; pp. 1-4.
Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.
Horseman, Samantha, et al.; "Gamefication of Health, Safety and the Environment {HSE): An Avatarial Solution" American Society of Safety Engineers 11th Professional Development Conference & Exhibition, Bahrain, Mar. 2014;pp. 1-10.
Index for "Micro-NanoMechatronics and Human Science (MHS), 2010 International Symposium Nov. 2010", retrieved from <http://ieeexplore.ieee.org/xpl/mostRecentIssuejsp?punumber=5658189> Ma 7, 2012. (pp. 1-5).
International Preliminary Report on Patentability for International Application No. PCT/US2012/045395, dated Jan. 7, 2014. (pp. 1-12).
International Preliminary Report on Patentability for International Application No. PCT/US2012/045401 dated Jan. 7, 2014. (pp. 1-9).
International Preliminary Report on Patentability for International Application No. PCT/US2012/045407 dated Jan. 7, 2014. (pp. 1-8).
International Preliminary Report on Patentability for International Application No. PCT/US2012/045410 dated Jan. 7, 2014. (pp. 1-8).
International Preliminary Report on Patentability for International Application No. PCT/US2012/045414 dated Jan. 7, 2014. (pp. 1-8).
International Preliminary Report on Patentability for International Application No. PCT/US2012/045419 dated Jan. 7, 2014. (pp. 1-11).
International Preliminary Report on Patentability for International Application No. PCT/US2012/045427 dated Jan. 7, 2014. (pp. 1-10).
International Preliminary Report on Patentability for International Application No. PCT/US2012/045435 dated Jan. 7, 2014. (pp. 1-10).
International Preliminary Report on Patentability for International Application No. PCT/US2012/045442 dated Jan. 7, 2014. (pp. 1-10).
International Preliminary Report on Patentability for International Application No. PCT/US2012/045447 dated Jan. 7, 2014. (pp. 1-8).
International Preliminary Report on Patentability for International Application No. PCT/US2012/045452 dated Jan. 7, 2014. (pp. 1-9).
International Search Report & Written Opinion for International Application No. PCT/US2012/045401, dated Feb. 5, 2013. (pp. 1-13).
International Search Report & Written Opinion for International Application No. PCT/US20121045407, dated Jan. 23, 2013. (pp. 1-15).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045447, dated Jan. 18, 2013. (pp. 1-12).
International Search Report and Written Opinion for International Application No. PCT/US2004/045442, dated Nov. 7, 2012, pp. 1-14.
International Search Report and Written Opinion for International Application No. PCT/US2012/045395, dated Dec. 3, 2012, pp. 1-16.
International Search Report and Written Opinion for International Application No. PCT/US2012/045419, dated Dec. 6, 2012, pp. 1-16.

(56) References Cited

OTHER PUBLICATIONS

International Search Report and Written Opinion for International Application No. PCT/US2012/045427, dated Dec. 3, 2012, pp. 1-14.
International Search Report and Written Opinion for International Application No. PCT/US2012/045452, dated Dec. 3, 2012, pp. 1-14.
International Search Report and Written Opinion for PCT/US2014/056427 dated Apr. 22, 2015.
International Search Report and Written Opinion for PCT/US2014/069498 dated Apr. 1, 2015.
Ivanoff, Jason, Philip Branning, and René Marois. "fMRI evidence for a dual process account of the speed-accuracy tradeoff in decision-making." PLoS one 3.7 (2008): e2635. pp. 1-14.
Jamison, Dean T., et al.; "The World Health Report 1999" World Health Organization, WHO Library Cataloguing in Publication Data, 1999; pp. 1-136.
Johns, G., "Presenteeism in the Workplace: A review and research agenda", Journal of Organizational Behavior, Jul. 31, 2009, pp. 519-542.
Kelly et al. The Novartis Health Index: A Method for Valuing the Economic Impact of Risk Reduction in a Workforce—J Occup Environ Med. (JOEM) vol. 52, No. 5, dated May 2010; pp. 528-535.
Knikou, Maria. "The H-reflex as a probe: pathways and pitfalls." Journal of neuroscience methods 171.1 (2008): 1-12.
Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Lamkin, Paul; "The best VR headsets: Oculust Rift, PlayStation VR, Gear VR, HTC Vive . . . virtual reality is back baby" 10 Sep. 16, 2015; available as of 10/212015 at the website: http://www.wearable.com/headgear/the-best-ar-and-vrheadsets;pp. 1-1.
Marais, René, and Jason Ivanoff. "Capacity limits of information processing in the brain." Trends in cognitive sciences 9.6 (2005): 296-305.
Moreno, Roxana, and Alfred Valdez. "Cognitive load and learning effects of having students organize pictures and words in multimedia environments: The role of student interactivity and feedback." Educational Technology Research and Development (2005).
Moreno, Roxana, and Richard Mayer. "Interactive multimodal learning environments." Educational Psychology Review 19.3 (2007): 309-326.
Moreno, Roxana. "Learning in high-tech and multimedia environments." Current directions in psychological science 15.2 (2006): 63-67.
Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.
Nintendo of America Inc., Wii Balance Board Operations Manual, 2008, pp. 1-10.
Nintendo of America Inc., Wii Fit Instruction Booklet, 2008, pp. 1-28.
Nintendo Wii Fit, https://www.youtube.com/watch?v=-Taruqvk30E, May 11, 2008.
Ovans, Andrea; What Resilience Means, and Why it Matters Harvard Business Review Jan. 5, 2015; pp. 1-6.
Priya, S., "Advances in Energy Harvesting Using Low Profile Piezoelectric Transducers", Materials Science & Engineering, Springer, Mar. 2007, pp. 165-182.
Prochaska et al. 'The Well-Being Assessment for Productivity'—J Occup Environ Med. (JOEM) vol. 53, No. 7, dated Jul. 2011; pp. 735-768.
Qlik Technology Partners available as of Oct. 21, 2015 at the website: http://www.qlik.com/us/partners/technologypartners;pp. 1-21.
Quick, James Campbell, et al. "Executive health: Building strength, managing risks" Academy of Management Executive, May 2000, vol. 14, No. 2, pp. 33-45.
Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.
Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.
Ready, Douglas A., et al.; "Are You a High Potential?" Harvard Business Review Jun. 2010; pp. 1-13.
Reidel, J.E., Baase, C., "The effect of disease prevention & health promotion on worksite productivity: a literature review", American Journal of Health Promotion, 15:3, Jan./Feb. 2001, pp. 167-191, 243.
Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.
Roberts, R.O.,Bergstralh, E.J., Schmidt, L, Jacobsoen,S.J., "Comparison of Self Reported and Medical Record Health Care Utilization Measures", Journal of Clinical Epidemiology, 49:9, Feb. 1996, pp. 989-995.
Rosen, Yigal. "The effects of an animation-based on-line learning environment on transfer of knowledge and on motivation for science and technology learning." Journal of Educational Computing Research 40.4 (2009): 451-467.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Simmonds, Bethany, et al. "Objectively assessed physical activity and subsequent health service use of UK adults aged 70 and over: A four to five year follow up study." PloS one 9.5 (2014): e97676.
Slater et al., "Taking Steps: The Influence of a Walking Technique on Presence in Virtual Reality", ACM Transactions on Computer-Human Interaction, Sep. 1995, pp. 201-219, vol. 2 No. 3.
Spisak, Brian R., et al., "A face for all seasons: Searching for context-specific leadership traits and discovering a general preference for perceived health" Frontiers in Human Neuroscience; Nov. 5, 2014.
Sullivan 'Making the Business Case for Health and Productivity Management'—J Occup Environ Med. (JOEM) vol. 16, No. 6 suppl, dated Jun. 2004; pp. S56-S61.
The American Heritage Dictionary of the English Language, definition of planar, 2000.
The constitution of the World Health Organization, World Health Organization, WHO Chronicle, 1947, pp. 1-202.
Veeva Systems and Zinc Ahead Join Forces available as of Oct. 2, 2015 at the website: http://www.veeva.com; pp. 1-6.
Wang, Xiaoning. "An Empirical Study of Optimizing Cognitive Load in Multimedia Integrated English Teaching." Studies in Literature and Language 9.3 (2014): 70.
Withings, The Internet connected Body Scale, retrieved with the Wayback Machine using link at www.withings.com, Jan. 11, 2010.
World Economic Forum 'The Workplace Wellness Alliance—Making the Right Investment: Employee Health and the Power of Metrics' dated Jan. 2013; pp. 1-35.
"40 Best Companies for Leaders—2014" Chief Executive, available as of Dec. 13, 2015 at the website: http://chiefexecutive.net/40-best-companies-for-leaders-2014/; (pp. 1-3).
"Augmented Reality", retrieved from <http://en.wikipedia.org/wiki/Augmented_reality>, May 30, 2012. pp. 1-18.
"Biofeedback—MayoClinic.com", retrieved from <http://www.mayoclinic.com/health/biofeedback/MY01072>, May 7, 2012. (pp. 1-2).
"Cardinus Risk Management | Ergonomic & DSE Risk Assessments", retrieved from <http://www.cardinus.com/>, Sep. 12, 2012. (pp. 1-2).

(56) References Cited

OTHER PUBLICATIONS

"Chronic diseases and health promotion" Centers for Disease Control and Prevention, 2011, <http://www.cdc.gov/chronicdisease/overview> [Accessed Feb. 2, 2011].
"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).
"Electroencephalography (EEG)", retieved from <http://www.emedicinehealth.com/script/main/art.asp?articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).
"EmotivEPOC Software Devlopment Kit", retrieved from <www.emotiv.com/store/hardware/epoc-bci-eeg/developer-neuroheadset/>, Jun. 11, 2012. (pp. 1-2).
"Kinect—Xbox.com", retrieved from <http://www.xbox.com/en-US/kinect>, Jun. 11, 2012. (pp. 1-3).
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Murray Hill, WellMed Team to Offer Next Generation Online Preventive Health Services" ProQuest, PR Newswire, New York, Nov. 3, 1999, 3 pages.
"National Health Expenditure Data", Centers for Medicare & Medicaid Services, available at: <https://www.cms.gov/Research-Statistics-Data-and-Systems/Statistics-Trends-and-Reports/NationalHealthExpendData/index.html>, accessed Nov. 18, 2013, pp. 1-2.
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"Research programs—Philips Research", retrieved from <http://www.research.philips.com/programs/index.html>, May 7, 2012. (pp. 1-2).
"RJL Systems, Products", retrieved from <http://www.rjlsystems.com/products.shtml>, May 7, 2012. (p. 1).
"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Productsidevices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo in Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, 1 page, XP002456414.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195x/abstract>, May 7, 2012. (p. 1).
Aldana, S., "Financial Impact of health promotion programs: a comprehensive review of the literature", American Journal of Health Promotion,155, 2001, pp. 296-320.
Aldana, S., Merrill, R., Price, K, Hardy, A., and Hager, R., "Financial impact of a comprehensive multi-site worksite health promotion program", Preventive Medicine, 40, Jul. 2004, pp. 131-137.
Alfredo Vazquez Carazo, "Novel Piezoelectric Transducers for High Voltage Measurements", Jan. 2000, pp. 1-277.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Asplund, Christopher L., et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 25.3 (2014): 824-831.
Baicker, K., Cutler, D., Song, Z., "Worksite wellness programs can generate savings", Health Affairs 29(2), Jan. 2010, pp. 1-8.
Bed-Check Co., Bed-Check Monitoring Systems, 2006.
Berger et al. 'Investing in Healthy Human Capital'—J Occup Environ Med. (JOEM) vol. 45, No. 12, dated Dec. 2003; pp. 1213-1225.
Berry, Leonard et al., "What's the Hard Return on Employee Wellness Programs?", Harvard Business Review, Dec. 2010. (pp. 1-10).
Borah, J. "Conceptual modeling—The missing link of simulation development." Proceedings of the 2002 Spring Simulation Conference. 2002. AEgis Technologies Group; pp. 1-7.

| Company | Product | Advantages |
|---|---|---|
| A123Systems | Lithium-ion battery with the cathode made from nano-phosphate, literature is unclear as to whether this is nanoparticles of phosphate on a substrate or a nano-porous phosphate structure | Higher power, quicker recharge, less combustible than standard lithium-ion batteries |
| Mphase Technologies | Battery with chemicals isolated from electrode by "nanograss" when the battery is not in use | Very long shelf life |
| Altairenano | Lithium-ion battery with the anode composed of lithium titanate spindel nanoparticles | Higher power, quicker recharge, less combustible than standard lithium-ion batteries |
| Zpower | Silver-zinc battery using nanoparticles in the silver cathode | Higher power density, low combustibility |

FIG. 19

Table 1: Most common lethal cardiac problems

| Condition | Car Analogy | Caused by | Typical time to death |
|---|---|---|---|
| Myocardial infarction (heart attack) | Fuel problem | Blocked artery | 1 minute to 1 year |
| Cardiac arrest | Electrical problem | Typically ventricular fibrillation | 5-10 seconds |
| Heart failure | Engine wearing out | Typically nonfatal heart attack | 5-10 years |

FIG. 20
(Prior Art)

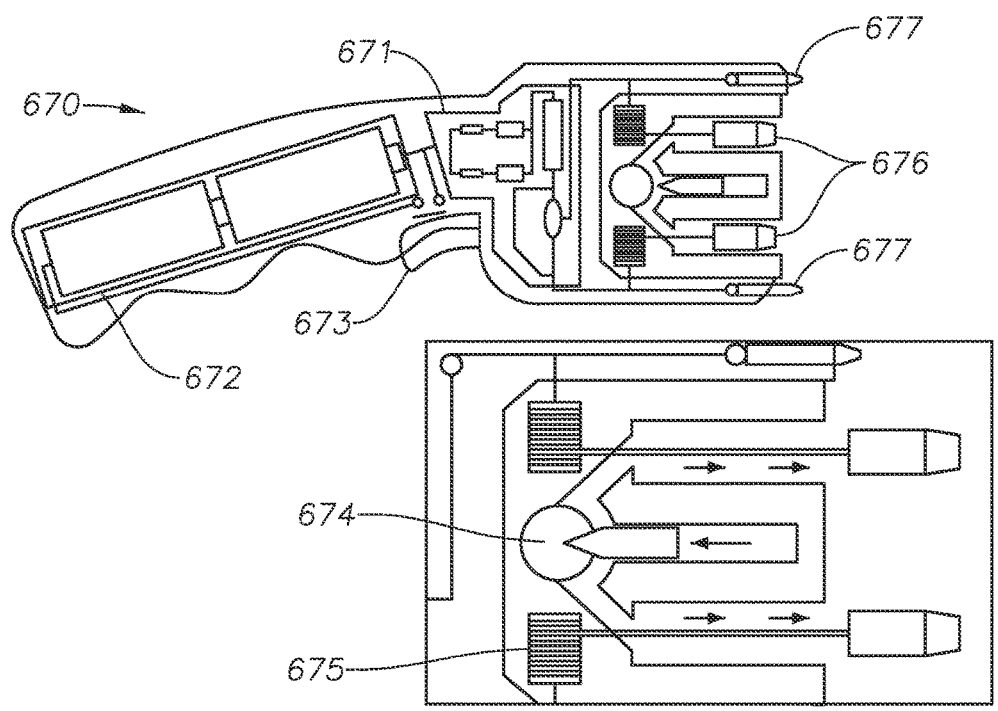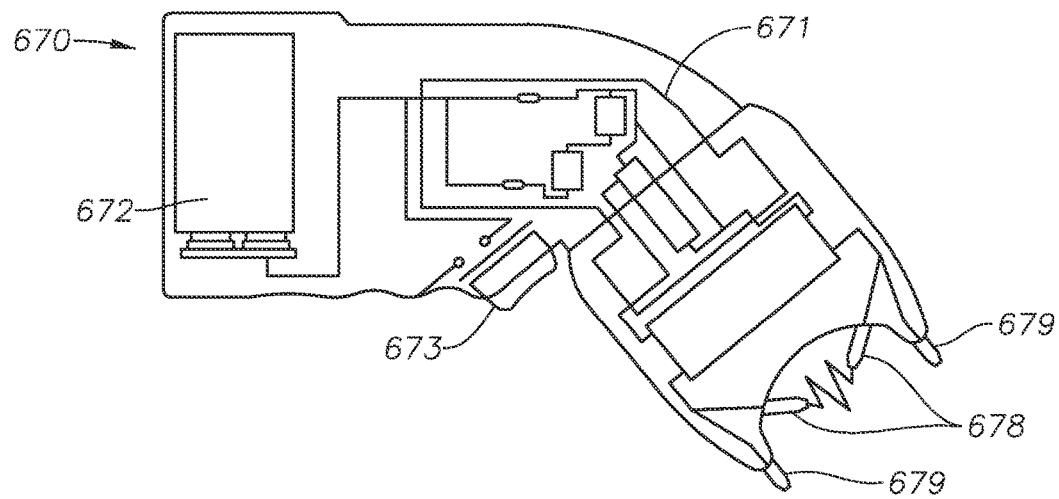
FIG. 21

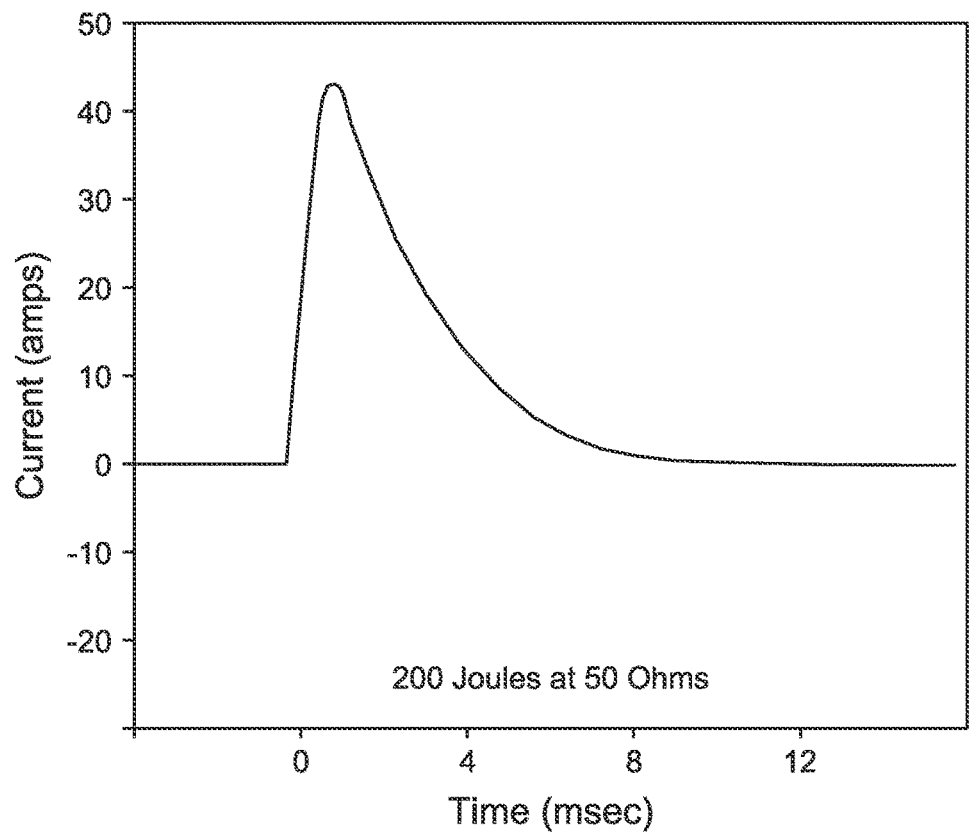
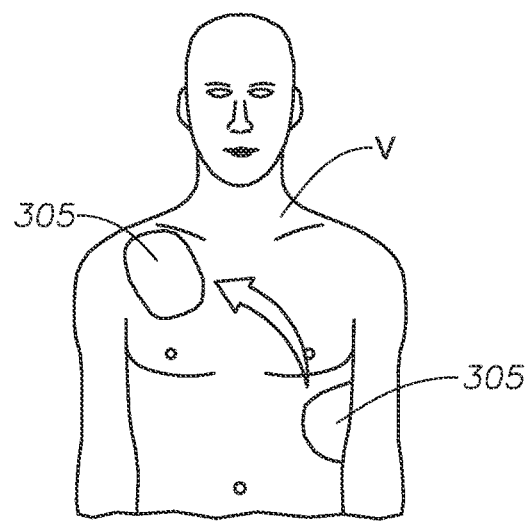
FIG. 23

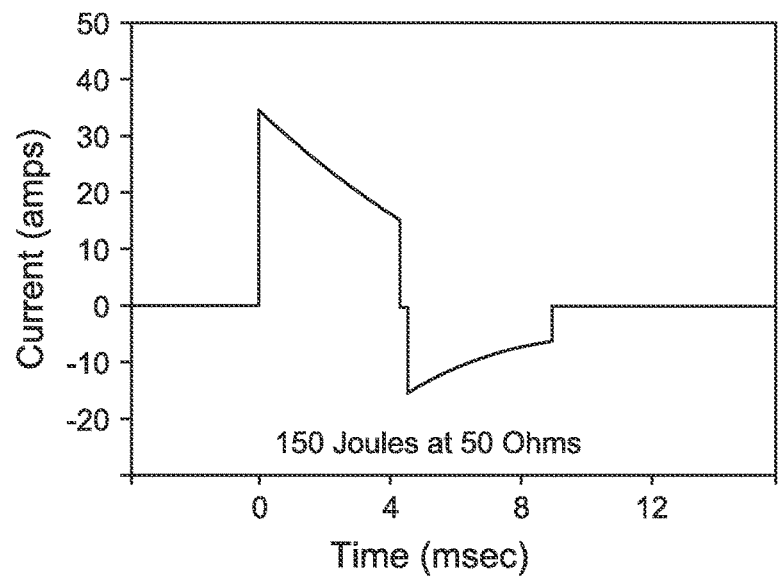
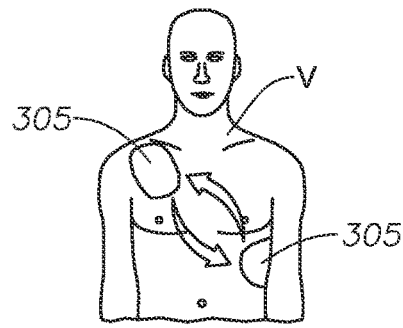
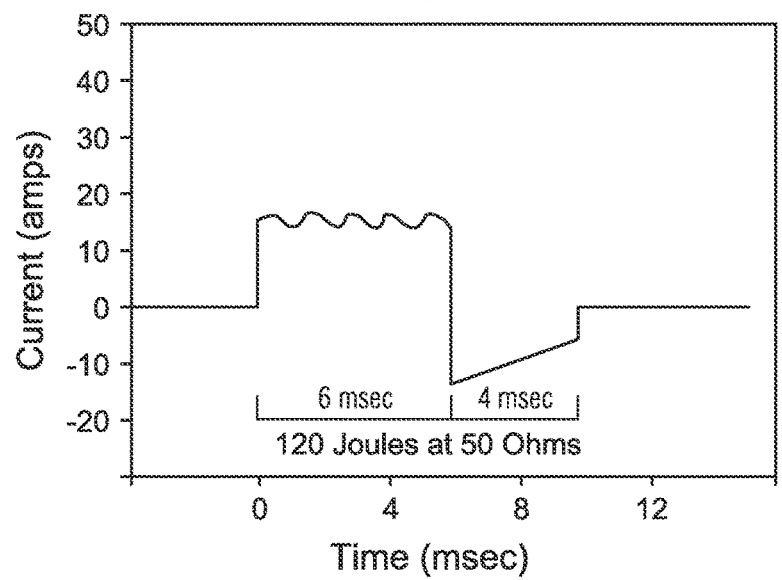
FIG. 24

SYSTEMS, PROTECTIVE CASINGS FOR SMARTPHONES, AND ASSOCIATED METHODS TO ENHANCE USE OF AN AUTOMATED EXTERNAL DEFIBRILLATOR (AED) DEVICE

FIELD OF THE INVENTION

Embodiments of the invention relate to medical devices and, more specifically, to systems, protective casings for smartphones, and associated methods to enhance use of an automated external defibrillation (AED) device.

BACKGROUND OF THE INVENTION

Between 300,000 and 400,000 deaths per year in the United States result from cardiac arrest. Further, most cardiac arrest deaths occur outside the hospital. In fact, current out-of-hospital survival rates are one to five percent (1-5%). In 1999 and 2000, for example, cardiac arrest caused 815 of 6,339 workplace fatalities reported to the Occupational Health and Safety Administration (OSHA). Abnormal heart rhythms cause cardiac arrest, and ventricular fibrillation (VF or V-Fib) is the most common of these abnormal rhythms. VF is a heart condition in which the heart quivers instead of mechanically pumping blood throughout the body and thus causes the heart to stop circulating blood. The most effective treatment for VF is administering CPR followed by use of a defibrillator as soon as it is available. Treatment of VF with immediate electronic defibrillation may increase survival to more than ninety percent (90%). But with each minute of delay in defibrillation, ten percent (10%) fewer victims survive.

An automated external defibrillator (AED) may be designed to allow anyone to use the defibrillator regardless of whether the user has been formally trained on its operations. AEDs may accomplish this through the use of voice instructions, pictures, and prompts, for example. An AED may only deliver a shock if indicated, and AEDs may be nonhazardous when used correctly. AEDs may improve survival after an out-of-hospital cardiac arrest because use of AEDs may reduce the critical time for treatment. That is, less time between the cardiac incident and defibrillation may improve the victim's chances of survival. For example, defibrillation within three minutes of sudden cardiac arrest (SCA) increases the chances of the SCA victim's survival to seventy percent (70%). Further, defibrillation within one minute of collapse raises the survival rate to ninety percent (90%). Laws and regulations may recommend or require AEDs in various locations (e.g., a workplace), but defibrillation may be delayed as a result of the time it takes to locate a nearby fixed AED. In addition, many locations do not have available AEDs. Frequently, calling emergency medical services (EMS) is necessary, but the wait for first responders may take too long. For example, the average call-to-shock time in a typical community is nine minutes. Time is crucial in an SCA, and there may only be minutes between life and death. CPR may only buy a little more time, potentially giving the victim a small amount of extra time until a defibrillator arrives. However, SCA ultimately requires a shock to restore a normal heart rhythm. As a result, CPR and heart saving training also may include AED training. An AED does not restart the heart or fix a "flat line," however, because a flat line represents that there is no heart electrical activity at all. That is, a flat line often represents clinical death because it is rare to recover from a flat line rhythm. Consequently, an AED attempts to correct the electrical system of the heart that is malfunctioning rather than to jump start it. If an AED recognizes a "flat line," it may indicate that no shock is advised and instruct the user to resume CPR because shocking a flat line does not benefit the victim.

In the workplace, thirteen percent (13%) of all workplace fatalities stem from SCA, which is the leading cause of death in the United States. For example, death from SCA in the United States is 96 times more likely than death from fire. Nevertheless, many entities have a sufficient number of fire extinguishers in place to protect their employees, customers, and visitors but nevertheless severely lack installed AEDs. However, having AEDs readily available in the workplace, along with training and installation policies and programs, may mean the difference between life and death. The American Heart Association (AHA) strongly supports having AEDs in public areas such as sports arenas, office complexes, schools, doctors' offices, shopping malls, airports, and other public places. The AHA also advocates that all police, fire, and rescue vehicles be equipped with an AED. Availability of AEDs may be important because use of an AED is an immediate action that may be required to save any victim undergoing an SCA. An AED may be operated successfully by any bystander, who does not need to be medically trained, in any emergent situation, such as a public place, school, office, and communities alike. In fact, victims of SCA who are treated with AEDs by bystanders are much more likely to survive.

SCA takes the lives of 400,000 people per year. During SCA, the heart's normal heart rhythm suddenly may become chaotic. The heart is no longer able to pump blood effectively, and the victim may collapse, stop breathing, become unresponsive, and have no detectable pulse. SCA may strike anyone at any time, including people of a variety of ages and fitness levels. That is, children, teenagers, athletes, and elderly individuals all may experience SCA. Although the risk of SCA increases with age and with a history of heart problems, a large percentage of SCA victims are people with no known risk factors. Further, SCA is different from a heart attack, i.e., a myocardial infarction. In simple terms, SCA is an electrical problem, whereas a heart attack is a "plumbing" problem, as described in the table illustrated in FIG. 20, for example. In some cases a heart attack, which itself may not be fatal, actually may trigger SCA. The globally recognized treatment for SCA is defibrillation, and it is the only treatment proven to restore a normal heart rhythm. When used on a victim of SCA, an AED may be used to administer a lifesaving electric shock that restores the heart's rhythm to normal. But although AEDs may be designed to allow non-medical personnel to save lives, AED machines may not be installed everywhere and often take extra time to locate and bring to any emergency situation.

One study found that overall survival to hospital discharge from 13,769 cardiac arrests was seven percent (7%). However the survival rate increased to nine percent (9%) for victims who received bystander CPR, twenty-four percent (24%) for those who had an AED applied before EMS personnel arrived, and thirty-eight percent (38%) for those who received an AED shock before EMS arrival. After adjusting for age, sex, bystander CPR, arrest location, EMS response time, witness status, initial rhythm, and study site, the study found that AED application was associated with a greater likelihood of survival (OR 1.75, 95% CI 1.23 to 1.50). More specifically, to assess the clinical and public health impact of investment in AEDs, which sell at a rate of about 200,000 per year, the study used data from the Resuscitation Outcomes Consortium (ROC), which encompasses 215 EMS agencies in seven sites in the United States and three in Canada. The ROC Epistry Cardiac Arrest registry records information on non-traumatic out-of-hospital cardiac arrests. The study analysis included 13,769 cardiac arrests that were not witnessed by EMS personnel. Of those, 2.1% had an AED applied before EMS arrival. That rate ranged from 1% to 7% between sites. The AED was applied by lay volunteers in 35% of the cases, by healthcare workers in 32%, by police in 26%, and by unknown bystanders in 7%. Survival was highest following an AED application by a lay volunteer (40%), followed by healthcare workers (16%) and police (13%), which demonstrates the greater importance of speed compared to training. In a post hoc analysis, absolute survival rates were higher in public sites (35% with AED application and 20% without) than in private locations (9% with AED application and 6% without). However, after multivariable adjustment there was no significant interaction between arrest location and survival (P=0.53). The researchers extrapolated their findings from the population served by the ROC, which was about 21 million people, to the combined population of the United States and Canada, which is about 330 million people, and estimated that AED application to victims of out-of-hospital cardiac arrest by bystanders saves about 474 lives per year.

AEDs may be nonhazardous to use by anyone who has been shown how to use an AED. In fact, some AEDs include voice guidance to guide a rescuer through the steps involved in saving someone, e.g., "apply pads to the victim's bare chest" and "press the red shock button." In addition, the pads themselves may have pictures of where they should be placed. Furthermore, safeguards sometimes have been designed into AEDs to ensure that non-medical responders may not use the AED to shock someone who does not need a shock.

AEDs may come with a lithium battery pack, which may have 5- or 7-year lifespan, for example. If the AED is used frequently, however, the battery pack may have to be replaced more often. In addition, an AED may inform an end user when the battery pack needs to be replaced. Further, an electrode pad package may need to be replaced every two years. An AED may perform automatic self-checks on a daily basis to test its operational readiness. If anything is not fully functional, the unit may initiate an alert with a loud chirp and flash a red light to warn that service may be required.

SUMMARY OF THE INVENTION

Automated external defibrillator (AED) devices can be used to deliver a shock to victims of sudden cardiac arrest (SCA) to restore normal rhythm to the heart. The effectiveness of defibrillation, however, can be time-sensitive. Victims of SCA who receive defibrillation within three minutes of the SCA have a 70% survival rate. But when defibrillation occurs ten minutes after the SCA, the survival rate is nearly zero. Even laypeople without medical training can use AEDs, and AEDs are available in many public places. However, AEDs are not available everywhere and sometimes are not readily accessible within the time period necessary for use of an AED to be effective. Applicant has recognized that not every building, roadside, sporting event, or family outing has an installed AED machine within reach and that, in cases of emergency, an AED can be unavailable quickly enough to save a life. Further, Applicant has recognized that some workplaces, including those associated with shift work, high stress, and exposure to certain chemicals and electrical hazards, can increase the risks of heart disease and cardiac arrest, as well. Having recognized that, in some cases, AEDs would be more widely used and therefore potentially save more lives if they were more portable, traceable, and mobile, embodiments of the invention can include systems, protective casings for smartphones, and associated methods to enhance use of an automated external defibrillator (AED) device before arrival of emergency medical personnel.

Immediately applying an AED when a person's heart stops beating can double or even triple that person's chances of survival. However, bystanders often do not know how to respond to a medical emergency. Embodiments of the invention can provide solutions to this problem making AEDs available everywhere and at any scene by providing an AED that is as portable and convenient as mobile phone. Further, embodiments of the invention can enable early defibrillation to be a part of any emergency response plans and can improve Emergency Medical Services (EMS) response to remote, diverse, and underserved areas.

For example, an embodiment of the invention can include a system to enhance use of an automated external defibrillator (AED) device before arrival of emergency medical personnel. A system according to an embodiment, for example, can include a mobile phone configured to communicate with the Internet thereby to define a smartphone. A smartphone can be configured to include one or more processors thereby to define smartphone processors. A smartphone also can include one or more input and output units in communication with the smartphone processors and further in communication with one or more communication networks. Further, a smartphone can include one or more displays in communication with the smartphone processors and one or more speakers in communication with the smartphone processors. Still further, a smartphone can include one or more microphones in communication with the smartphone processors and non-transitory memory medium in communication with the smartphone processors and configured to include one or more smartphone modules. Each of the smartphone modules can include computer-readable instructions stored in the computer-readable medium that when executed by the smartphone processors cause the smartphone processors to perform operations. For example, the one or more smartphone modules can include a defibrillation control module to control defibrillation of a victim. A system also can include a protective casing abuttingly contacting one or more side portions of the smartphone and retaining the smartphone positioned therein. A protective casing can be configured to include, for example, one or more processors thereby to define casing processors, as well as one or more input and output units in communication with the casing processors and further in communication with the smartphone processors. A protective casing also can include one or more sensors in communication with the casing processors, one or more capacitors in communication with the casing processors, and two or more extendable electrode pads in communication with the casing processors and configured to transmit a current responsive to activation of the one or more capacitors. Further, a protective casing can include non-transitory memory medium in communication with the casing processors and configured to include a plurality of casing modules. Each of the casing modules can include computer-readable instructions stored in the computer-readable medium of the protective casing that when executed by the casing processors cause the casing processors to perform operations. For example, the plurality of casing modules can include a check module to determine, by use of the two or more extendable electrode pads and the one or more sensors, whether the victim's heart rhythm requires an electrical shock to reestablish a normal heart rhythm responsive to the defibrillation control module. The plurality of casing modules also can include a space module to measure, by use of the one or more sensors, presence and amount of preselected materials relatively near the system thereby to define environmental data responsive to the check module. Further, the plurality of casing modules can include a shock module to activate the one or more capacitors and generate an electrical current between the two or more extendable electrode pads to deliver an electrical shock to the victim's chest by use of the two or more extendable electrode pads responsive to the check module, the space module, and the defibrillation control module.

In some circumstances, the two or more extendable electrode pads can include a layer of nanomaterials on each surface of the two or more extendable electrode pads adapted to be positioned on the victim thereby to define two or more extendable electrode nano-coated pads. Further, operations of the check module can include measuring, by use of the two or more extendable electrode pads and the one or more sensors, impedance of a victim's body and determining, responsive to a determination that the victim's heart rhythm requires an electrical shock to reestablish a normal heart rhythm, an electrical shock energy level required to reestablish a normal heart rhythm to the victim's heart. Additionally, the preselected materials can include one or more of the following: oxygen, carbon monoxide, $H_2S$ emissions, gases, inflammables, and combustibles. The protective casing further can include a compartment adapted to house the two or more extendable electrode pads thereby to separate the two or more extendable electrode pads from one or more other components of the protective casing. The compartment can be a portion of a body of the protective casing, and the protective casing further can include a component that has one or more substantially rectangular faces, is connected to the body of the protective casing by one or more connections, and is adapted to substantially enclose the compartment when in a closed position thereby to define a compartment cover. The compartment cover can be adapted to enclose the two or more extendable electrode pads when in the closed position. In addition, the smartphone and the protective casing can be in communication through a Bluetooth connection. In some instances, the smartphone further can include one or more batteries, and the one or more batteries can provide power to charge the one or more capacitors. Further, the protective casing can include a direct current (DC) booster configured to amplify the power provided by the one or more batteries of the smartphone.

Additionally, the plurality of casing modules can include a sync module to generate an electrical current between the two or more extendable electrode pads in a synchronized cardio version, a pace module to transcutaneously pace the victim by use of the two or more extendable electrode pads, and a self-regulation module to determine when one or more components of the protective casing require replacement thereby to enable the protective casing to self-regulate. Likewise, the one or more smartphone modules further can include an augmented virtual reality (AVR) module to generate directions to use the system by use of the one or more displays and the one or more speakers and a rescue module to transmit geographical information systems (GIS) data associated with the system to emergency medical personnel via the one or more communication networks responsive to the defibrillation control module. Further, the one or more smartphone modules can include a record module to record biometric status of the victim from time of discovery to arrival of the emergency medical personnel thereby to enhance availability of telemedicine. The one or more smartphone modules also can include a note module to transcribe the recorded biometric status of the victim into medical notes for review by the emergency medical personnel responsive to the record module. Still further, the one or more smartphone modules can include an environmental module to transmit geographical positioning system (GPS) data associated with the system and the environmental data to the emergency medical personnel via the one or more communication networks, as well as an alert module to transmit data to the emergency medical personnel in real time via the one or more communication networks.

In some circumstances, each of the one or more smartphone modules can be associated with one or more applications of the smartphone, and the protective casing can be adapted to snap the smartphone into a locked position when the smartphone is positioned in the protective casing. Further, the protective casing can include an inner cavity that has five or more sides. Each of the five or more sides can be adapted to contact abuttingly one or more side portions of the smartphone when the smartphone is in the locked position. The protective casing also can be adapted to comply with OSHA standards.

An embodiment of the invention also can include a protective casing to enhance use of an automated external defibrillator (AED) device before arrival of emergency medical personnel. A protective casing according to an embodiment can be adapted to abuttingly contact one or more side portions of and retain a mobile phone configured to communicate with the Internet thereby to define a smartphone when the smartphone is positioned therein. Further, a protective casing can include one or more processors thereby to define casing processors and one or more input and output units in communication with the casing processors and further in communication with a smartphone. A protective casing also can include one or more sensors in communication with the casing processors, one or more capacitors in communication with the casing processors, and two or more extendable electrode pads in communication with the casing processors and configured to transmit a current responsive to activation of the one or more capacitors. Additionally, a protective casing can include non-transitory memory medium in communication with the casing processors and configured to include a plurality of modules. Each of the modules can include computer-readable instructions stored in the computer-readable medium that when executed by the casing processors cause the casing processors to perform operations. For example, the plurality of modules can include a check module to determine, by use of the two or more extendable electrode pads and the one or more sensors, whether the victim's heart rhythm requires an electrical shock to reestablish a normal heart rhythm responsive to input from the smartphone. The plurality of modules also can include a space module to measure, by use of the one or more sensors, presence and amount of preselected materials relatively near the protective casing thereby to define environmental data responsive to the check module. In addition, the plurality of modules can include a shock module to activate the one or more capacitors and generate an electrical current between the two or more extendable electrode pads to deliver an electrical shock to the victim's chest by use of the two or more extendable electrode pads responsive to the check module, the space module, and input from the smartphone.

In some circumstances, the two or more extendable electrode pads can include a layer of nanomaterials on each surface of the two or more extendable electrode pads adapted to be positioned on the victim thereby to define two or more extendable electrode nano-coated pads. Further, in some circumstances, operations of the check module can include measuring, by use of the two or more extendable electrode pads and the one or more sensors, impedance of a victim's body and determining, responsive to a determination that the victim's heart rhythm requires an electrical shock to reestablish a normal heart rhythm, an electrical shock energy level required to reestablish a normal heart rhythm to the victim's heart. Further, the preselected materials can include one or more of the following: oxygen, carbon monoxide, $H_2S$ emissions, gases, inflammables, and combustibles. The protective casing further can include a compartment adapted to house the two or more extendable electrode pads thereby to separate the two or more extendable electrode pads from one or more other components of the protective casing. The compartment can be a portion of a body of the protective casing. The protective casing further can include a component that has one or more substantially rectangular faces, is connected to the body of the protective casing by one or more connections, and is adapted to substantially enclose the compartment when in a closed position thereby to define a compartment cover. The compartment cover can be adapted to enclose the two or more extendable electrode pads when in the closed position. In addition, the protective casing can be in communication with the smartphone through a Bluetooth connection, and one or more batteries of the smartphone can provide power to charge the one or more capacitors. The protective casing also can include a direct current (DC) booster that is configured to amplify the power provided by the one or more batteries of the smartphone.

In some instances, the plurality of casing modules further can include a sync module to generate an electrical current between the two or more extendable electrode pads in a synchronized cardio version, a pace module to transcutaneously pace the victim by use of the two or more extendable electrode pads, and a self-regulation module to determine when one or more components of the protective casing require replacement thereby to enable the protective casing to self-regulate. The protective casing can be adapted to snap the smartphone into a locked position when the smartphone is positioned in the protective casing, and the protective casing can include an inner cavity that has five or more sides. Each of the five or more sides can be adapted to contact abuttingly one or more side portions of the smartphone when the smartphone is in the locked position. Further, the protective casing can be adapted to comply with OSHA standards.

An embodiment of the invention further can include a method to assemble a system to enhance use of an automated external defibrillator (AED) device before arrival of emergency medical personnel. For example, a method can include positioning a mobile phone configured to communicate with the Internet thereby to define a smartphone in a protective casing adapted to abuttingly contact one or more side portions of the smartphone and retain the smartphone. The protective casing can be configured to include one or more sensors, one or more capacitors, and two or more extendable electrode pads configured to transmit a current responsive to activation of the one or more capacitors.

An embodiment of the invention still further can include a method to use a protective casing for a mobile phone configured to communicate with the Internet thereby to define a smartphone to enhance use of an automated external defibrillator (AED) device before arrival of emergency medical personnel. The protective casing can be positioned to abuttingly contact one or more side portions of a smartphone and retain the smartphone. The protective casing can be configured to include one or more sensors, one or more capacitors, and two or more extendable electrode pads configured to transmit a current responsive to activation of the one or more capacitors. A method according to an embodiment can include positioning the two or more extendable electrode pads on a victim's chest. A method further can include determining, by use of the two or more extendable electrode pads and the one or more sensors, whether the victim's heart rhythm requires an electrical shock to reestablish a normal heart rhythm responsive to input from the smartphone. A method also can include measuring, by use of the one or more sensors, presence and amount of preselected materials relatively near the protective casing thereby to define environmental data responsive to determination of whether the victim's heart rhythm requires an electrical shock to reestablish a normal heart rhythm. In addition, a method can include activating the one or more capacitors responsive to measurement of presence and amount of the preselected materials relatively near the protective casing. A method further can include generating an electrical current between the two or more extendable electrode pads to deliver an electrical shock to the victim's chest by use of the two or more extendable electrode pads responsive to activation of the one or more capacitors.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

FIG. 19 is a table of battery properties according to an embodiment of the invention.

FIG. 20 is a table of cardiac conditions according to the prior art.

FIG. 21 is a schematic diagram of a system according to an embodiment of the invention.

FIG. 23 is a schematic diagram of a system and associated graph according to an embodiment of the invention.

FIG. 24 is a schematic diagram of a system and associated graphs according to an embodiment of the invention.

DETAILED DESCRIPTION OF THE INVENTION

So that the manner in which the features and advantages of the embodiments of systems, protective casings for smartphones, and associated methods of the present invention, as well as others, which will become apparent, may be understood in more detail, a more particular description of the embodiments of systems, protective casings for smartphones, and associated methods of the present invention briefly summarized above may be had by reference to the embodiments thereof, which are illustrated in the appended drawings, which form a part of this specification. It is to be noted, however, that the drawings illustrate only various embodiments of the embodiments of systems, protective casings for smartphones, and associated methods of the present invention and are therefore not to be considered limiting of the embodiments of systems, protective casings for smartphones, and associated methods of the present invention's scope as it may include other effective embodiments as well.

Embodiments of the invention can include systems, protective casings for smartphones, and associated methods to enhance use of an automated external defibrillator (AED) device before arrival of emergency medical personnel. For example, embodiments of the invention can include a more portable, traceable, and mobile solution that can be carried in a person's pocket or bag and further can even be the person's mobile phone, for example. Embodiments of the invention thus advantageously can provide the opportunity of "saving a life" everywhere. That is, phones can save lives. To create such a mobile device, embodiments of the invention can include the integration of augmented virtual reality (AVR) hardware and applications, designs similar to stun gun model designs to provide shock capabilities and to check heart rhythm of a victim, diagnostic ultrasound technologies, telemedicine (e.g., note-taking operations, record-keeping operations, rescue operations to provide information to EMS, bio-nanotechnology hardware and accessories, geographical information systems (GIS) to enhance rescue operations, geographical positioning systems (GPS) to assess the environment surrounding a victim, crowd sourcing, and signal enhancement technologies with real-time monitoring capabilities. Further, embodiments of the invention can include and combine: (1) hardware, (2) accessories, (3) applications (e.g., smartphone applications that can be downloaded), (4) a reporting system scorecard or dashboard, and (5) training solutions (e.g., avatar-based simulations and training, gamification).

Figure 1:
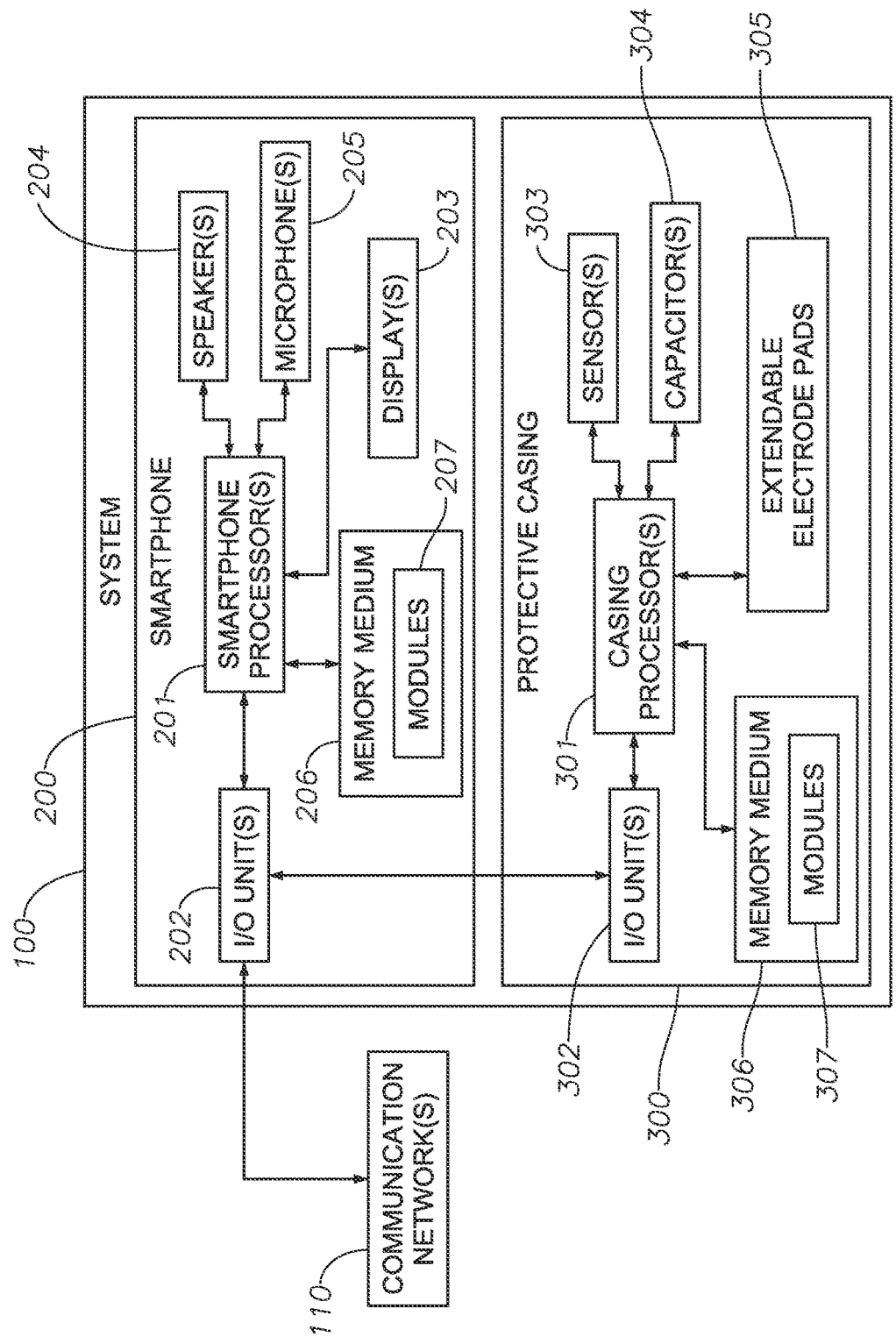
FIG. 1 is a schematic diagram of a system according to an embodiment of the invention.
Figure 2:
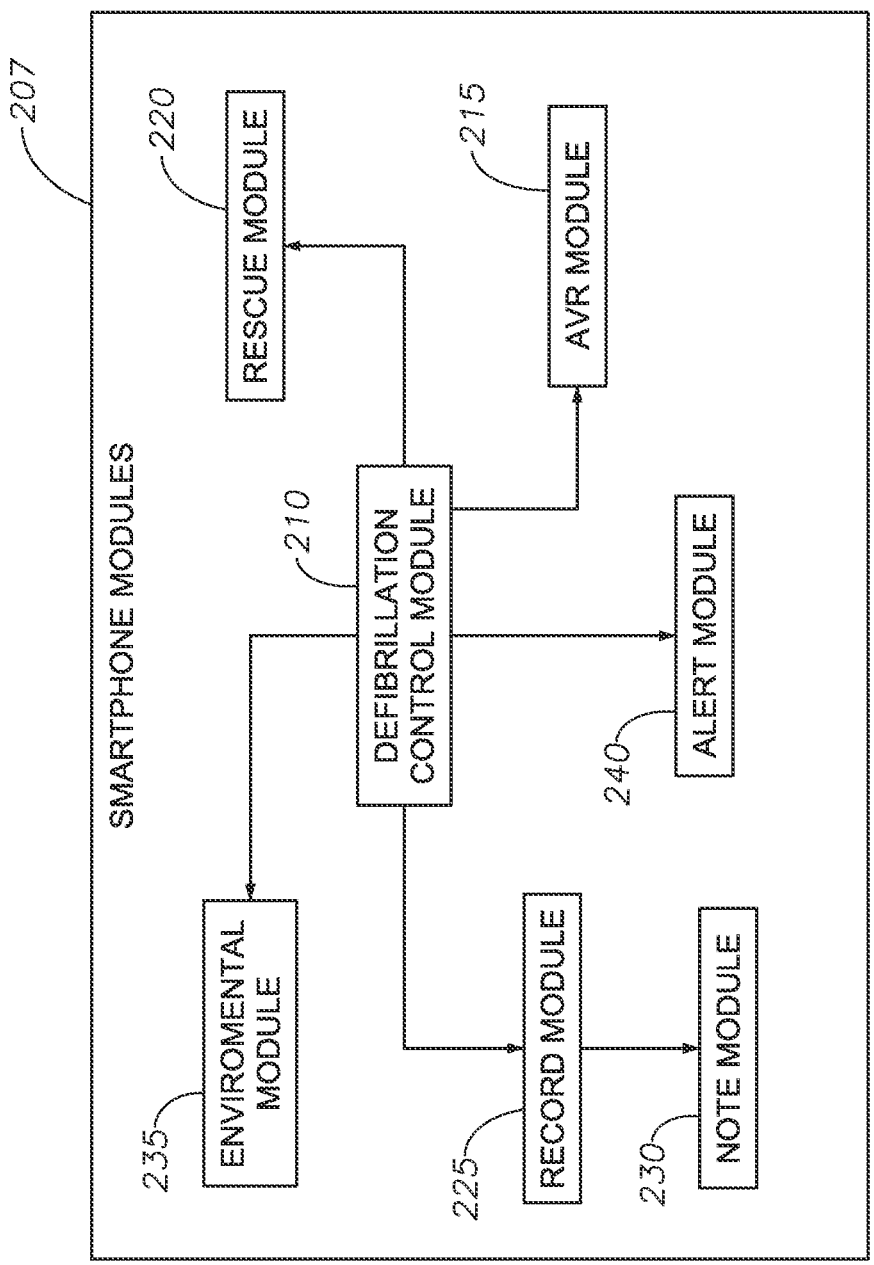
FIG. 2 is a schematic diagram of modules of a system according to an embodiment of the invention.

For example, a system 100 to enhance use of an automated external defibrillator (AED) device before arrival of emergency medical personnel according to an embodiment of the invention can include a mobile phone configured to communicate with the Internet thereby to define a smartphone 200, for instance, as illustrated in FIG. 1. A smartphone, which can be a mobile phone with an advanced operating system, can combine cellular phone capabilities with Internet access-based capabilities. Further, a smartphone can include, for example, email, photography, media content, and geolocation capabilities. Advantages of incorporating a smartphone 200 (in contrast to a traditional mobile phone) into a system 100 according to an embodiment can include that the capabilities of a smartphone 200 beyond those of a traditional mobile phone can enable additional capabilities of the system 100, as described in more detail below. The smartphone 200 can include, for example, one or more processors that can thereby define smartphone processors 201. The smartphone 200 further can include one or more input and output units 202 in communication with the smartphone processors 201. The one or more input and output units 202 also can be in communication with one or more communication networks 110. The smartphone 200 additionally can include one or more displays 203 in communication with the smartphone processors 201, for instance. Further, the smartphone 200 can include one or more speakers 204 in communication with the smartphone processors 201 and one or more microphones 205 in communication with the smartphone processors 201. The smartphone still further can include non-transitory memory medium 206 in communication with the smartphone processors 201. The non-transitory memory medium 206 also can be configured to include one or more modules thereby to define one or more smartphone modules 207, for example. Each of the smartphone modules 207 can include computer-readable instructions stored in the computer-readable medium 206 that—when executed by the smartphone processors 201—cause the smartphone processors 201 to perform operations. For example, the one or more smartphone modules 207 can include a defibrillation control module 210 to control defibrillation of a victim, as illustrated in FIG. 2, for instance. Defibrillation, as will be understood by those skilled in the art, can include applying a current to the victim's body by use of two or more electrodes thereby to force the current through the victim's heart, cause a shock to the quivering heart muscles, and consequently restore the heart's normal rhythm.

Figure 3:
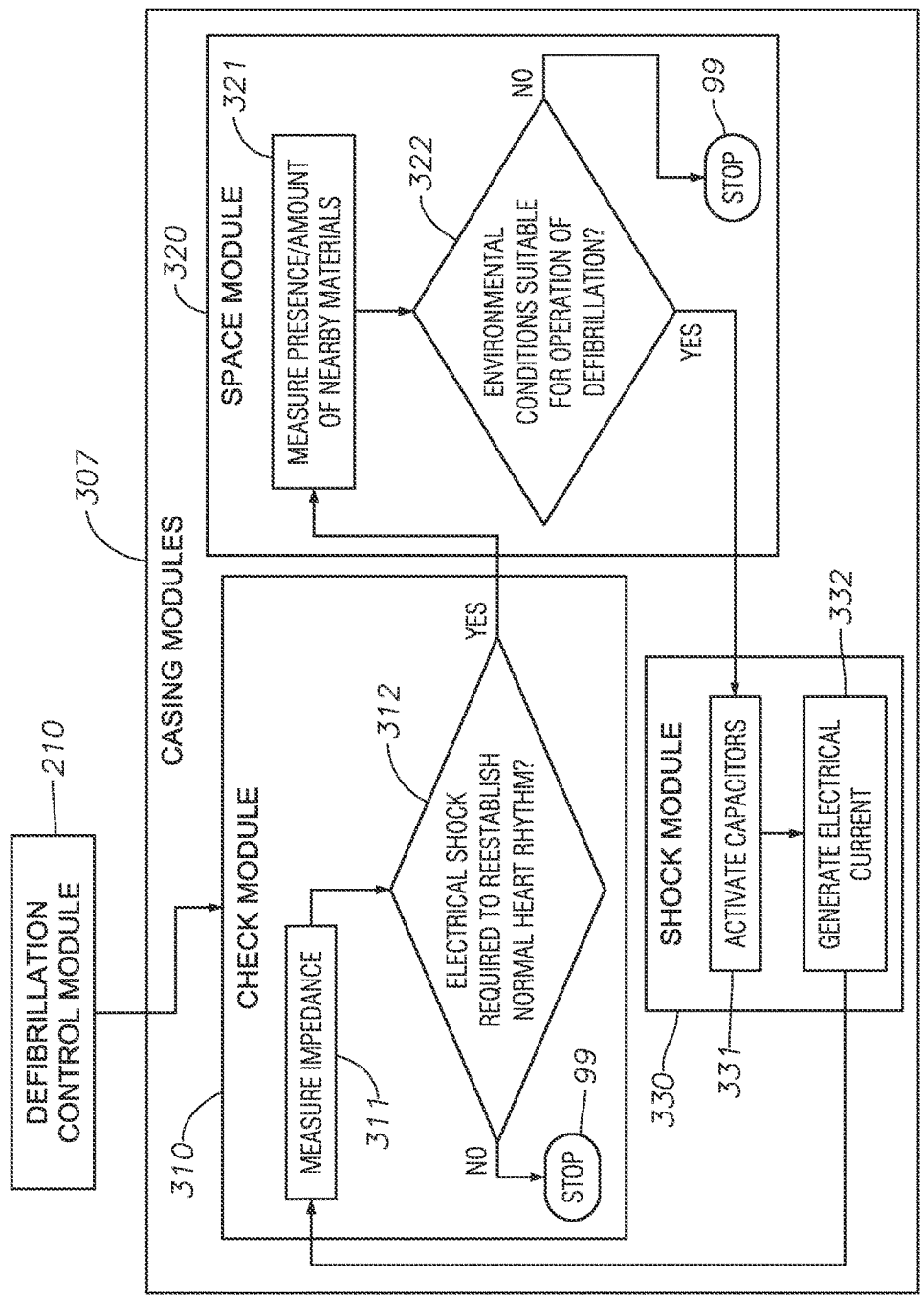
FIG. 3 is a schematic diagram of modules of a system according to an embodiment of the invention.

In addition to the smartphone 200, a system 100 according to an embodiment can include a protective casing 300. That is, an embodiment can be a combination of a smartphone 200 with a protective casing 300. A protective casing, as will be understood by those skilled in the art, can be a case or cover for a mobile phone that is designed to protect one or more components of the mobile phone from damage. For example, a protective casing 300 can be formed of one or more plastic components the reduce the likelihood that the smartphone 200 will be harmed if the smartphone 200 is dropped, for example. The protective casing 300 can abuttingly contact one or more side portions of the smartphone 200 and retain the smartphone 200 that is positioned therein, for example. In an exemplary configuration, for instance, the back of the smartphone 200 (that is, a side of the smartphone 200 that is opposite the one or more displays 203, for example) can be substantially parallel to and abuttingly contact an interior surface of the protective casing 300. In addition, the protective casing 300 can be configured to include one or more processors, which thereby can define casing processors 301. The protective casing 300 also can include one or more input and output units 302 in communication with the casing processors 301, and the one or more input and output units 302 further can be in communication with the smartphone processors 201. In addition, the protective casing 300 can include one or more sensors 303 in communication with the casing processors 301. The protective casing 300 also can include one or more capacitors 304 (e.g., nano-capacitors) in communication with the casing processors 301 and two or more extendable electrode pads 305 (e.g., nano-coated or nano-gel based pads) in communication with the casing processors 301. The two or more extendable electrode pads 305 can be configured to transmit a current responsive to activation of the one or more capacitors 304, for example. The protective casing 300 further can include non-transitory memory medium 306 in communication with the casing processors 301. The non-transitory memory medium 306 can be configured to include a plurality of modules thereby to define a plurality of casing modules 307, for example. Each of the casing modules 307 can include computer-readable instructions stored in the computer-readable medium 306 of the protective casing 300 that, when executed by the casing processors 301, cause the casing processors 301 to perform operations. The plurality of casing modules 307 can include, for example, a check module 310, a space module 320, and a shock module 330, as illustrated in FIG. 3, for example. The check module 310 can determine—by use of the two or more extendable electrode pads 305 and the one or more sensors 303—whether the victim's heart rhythm requires an electrical shock to reestablish a normal heart rhythm responsive to the defibrillation control module 210, as illustrated in FIG. 3, for example. That is, the check module 310 can check the status of the victim's heart. Operations of the check module 310 can include, for example, measuring impedance 311 and determining whether an electrical shock is required to reestablish a normal heart rhythm 312. If an electrical shock is not required 312, operations can include stopping 99. If an electrical shock is required 312, however, operations of the space module 320 can begin. The space module 320 can measure, by use of the one or more sensors 303, presence and amount of preselected materials relatively near the system 100 (that is, the space surrounding the system 100) thereby to define environmental data responsive to the check module 310. For example, operations of the space module 320 can include measuring presence and amount of nearby materials 321 then determining whether the environmental conditions are suitable for operation of defibrillation 322. If environmental conditions are unsuitable for operation of defibrillation 322, operations can include stopping 99. Environmental conditions could be unsuitable for operation if hazardous or flammable materials are present, for example. If environmental conditions are suitable for operation of defibrillation 322, however, operations of the shock module 330 can begin. The shock module 330 can activate the one or more capacitors 304 and generate an electrical current between the two or more extendable electrode pads 305 to deliver an electrical shock to the victim's chest by use of the two or more extendable electrode pads 305 responsive to the check module 310, the space module 320, and the defibrillation control module 210. That is, the shock module 330 can shock the victim. More specifically, the electric current between the two or more extendable electrode pads 305 can shock the victim, as will be understood by those skilled in the art. For example, operations of the shock module 320 can include activating the one or more capacitors 331 and generating an electrical current 332. After generating an electrical current 332, operations of the check module 310, e.g., measuring impedance 311, can begin again.

In some circumstances, the two or more extendable electrode pads 305 can include a layer of nanomaterials on each surface of the two or more extendable electrode pads 305 adapted to be positioned on the victim thereby to define two or more extendable electrode nano-coated pads. For example, stretchable nanomaterials, such as thin film or nano-skin, can be used. A sticky patch of such stretchable nanomaterials can be, for example, approximately 0.03 mm thick. A sticky patch of stretchable nanomaterials can coat the surfaces of the pads 305 that are placed in contact with the victim's chest, for example. In some circumstances, each of the pads 305 can be approximately 6 centimeters by 10 centimeters, for example.

Additionally, in some instances, operations of the check module 310 can include measuring, by use of the two or more extendable electrode pads 305 and the one or more sensors 303, impedance of a victim's body. Impedance, as will be understood by those skilled in the art, can indicate resistance, i.e., resistance to current flow. Resistance can exist in the electrical circuit itself as well as in the victim. The amount of impedance in a patient can be difficult to determine, however, because it can relate to body mass, temperature, diaphoresis, and quality of the contact with paddles or pads 305, for example. Impedance can be expressed in ohms. Operations of the check module 310 also can include determining, responsive to a determination that the victim's heart rhythm requires an electrical shock to reestablish a normal heart rhythm, an electrical shock energy level required to reestablish a normal heart rhythm to the victim's heart. In addition, the preselected materials can include one or more of the following: oxygen, carbon monoxide, $H_2S$ emissions, gases, inflammables, and combustibles.

Figure 13:
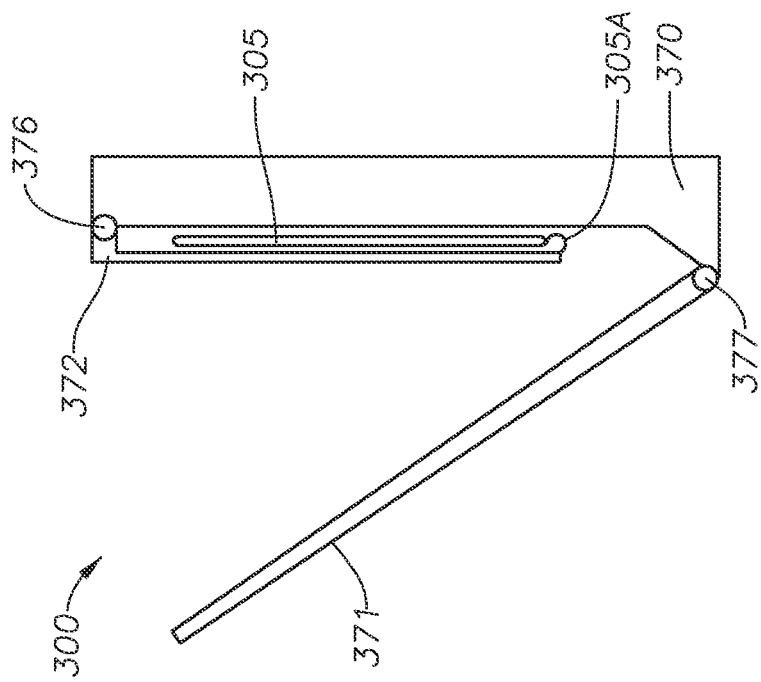
FIG. 13 is a schematic diagram of a protective casing according to an embodiment of the invention.

Further, the protective casing 300 can include a compartment adapted to house the two or more extendable electrode pads 305 thereby to separate the two or more extendable electrode pads 305 from one or more other components of the protective casing 300. An exemplary embodiment of a protective casing 300 is illustrated in FIG. 13, for example. In some circumstances, the compartment can be a portion of a body 370 of the protective casing 300. Further, the protective casing 300 can include a component that has one or more substantially rectangular faces, is connected to the body 370 of the protective casing 300 by one or more connections, such as hinges 377, and is adapted to substantially enclose the compartment when in a closed position thereby to define a compartment cover 371, for example. The compartment cover 371 thus can be adapted to enclose the two or more extendable electrode pads 305 when in the closed position.

Figure 15:
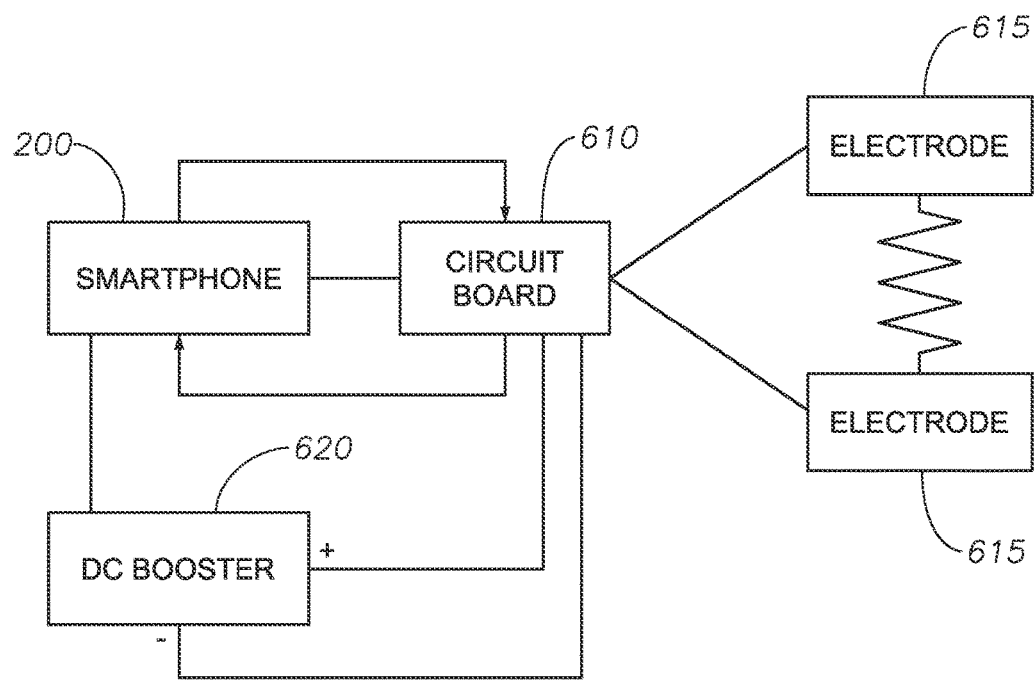
FIG. 15 is a schematic diagram of a system according to an embodiment of the invention.

In some circumstances, the smartphone 200 and the protective casing 300 can be in communication through a Bluetooth connection, for example. Additionally, the smartphone 200 further can include one or more batteries that can provide power to charge the one or more capacitors 304. The protective casing further can include a direct current (DC) booster 620 that is configured to amplify the power provided by the one or more batteries of the smartphone 200, as illustrated in FIG. 15, for example. In addition, the protective casing 300 can be adapted to snap the smartphone 200 into a locked position when the smartphone 200 is positioned in the protective casing 300, and the protective casing 300 can be adapted to comply with OSHA standards. The protective casing 300 can include an inner cavity that has five or more sides, and each of the five or more sides can be adapted to abuttingly contact one or more side portions of the smartphone 200 when the smartphone 200 is in the locked position.

In some instances, the plurality of casing modules 307 further can include a sync module to generate an electrical current between the two or more extendable electrode pads 305 in a synchronized cardioversion, as will be understood by those skilled in the art, and a pace module to transcutaneously pace the victim, as will be understood by those skilled in the art, by use of the two or more extendable electrode pads 305. The plurality of casing modules 307 still further can include a self-regulation module to determine when one or more components of the protective casing 300 require replacement thereby to enable the protective casing 300 to self-regulate. Self-regulation can include determining when one or more components require replacement or repair, for instance. Further, for example, self-regulation can occur daily, after an application or use, or responsive to prompts from a smartphone application, for example.

In addition, the one or more smartphone modules 207 further can include an augmented virtual reality (AVR) module 215 to generate directions to use the system 100 by use of the one or more displays 203 and the one or more speakers 204. The AVR module 215 thus can provide a user of the system 100 with a simulated experience with an instructor or coach for operation of the system 100. The one or more smartphone modules 207 also can include a rescue module 220 to transmit geographical information systems (GIS) data associated with the system 100 to emergency medical personnel via the one or more communication networks 110 responsive to the defibrillation control module 210. The rescue module 220 thus can enable rescue of the victim or assistance by emergency medical personnel. Still further, the one or more smartphone modules 207 can include a record module 225 to record biometric status of the victim from time of discovery to arrival of the emergency medical personnel thereby to enhance availability of telemedicine, for example. The one or more smartphone modules 207 also can include a note module 230 to transcribe the recorded biometric status of the victim into medical notes for review by the emergency medical personnel responsive to the record module 225. Operations thus can include electronic measuring and recording of all vital signs and diagnostic checks as a medical record ready for EMS on arrival or as real-time streaming to a medical facility. Additionally, the one or more smartphone modules 207 can include an environmental module 235 to transmit geographical positioning system (GPS) data associated with the system 100 and the environmental data to the emergency medical personnel via the one or more communication networks 110. The one or more smartphone modules 207 also can include an alert module 240 to transmit data to the emergency medical personnel in real time via the one or more communication networks 110. That is, an alert module 240 can alert emergency medical personnel in real time. In some instances, each of the one or more smartphone modules 207 can be associated with one or more applications of the smartphone 200.

Figure 14:
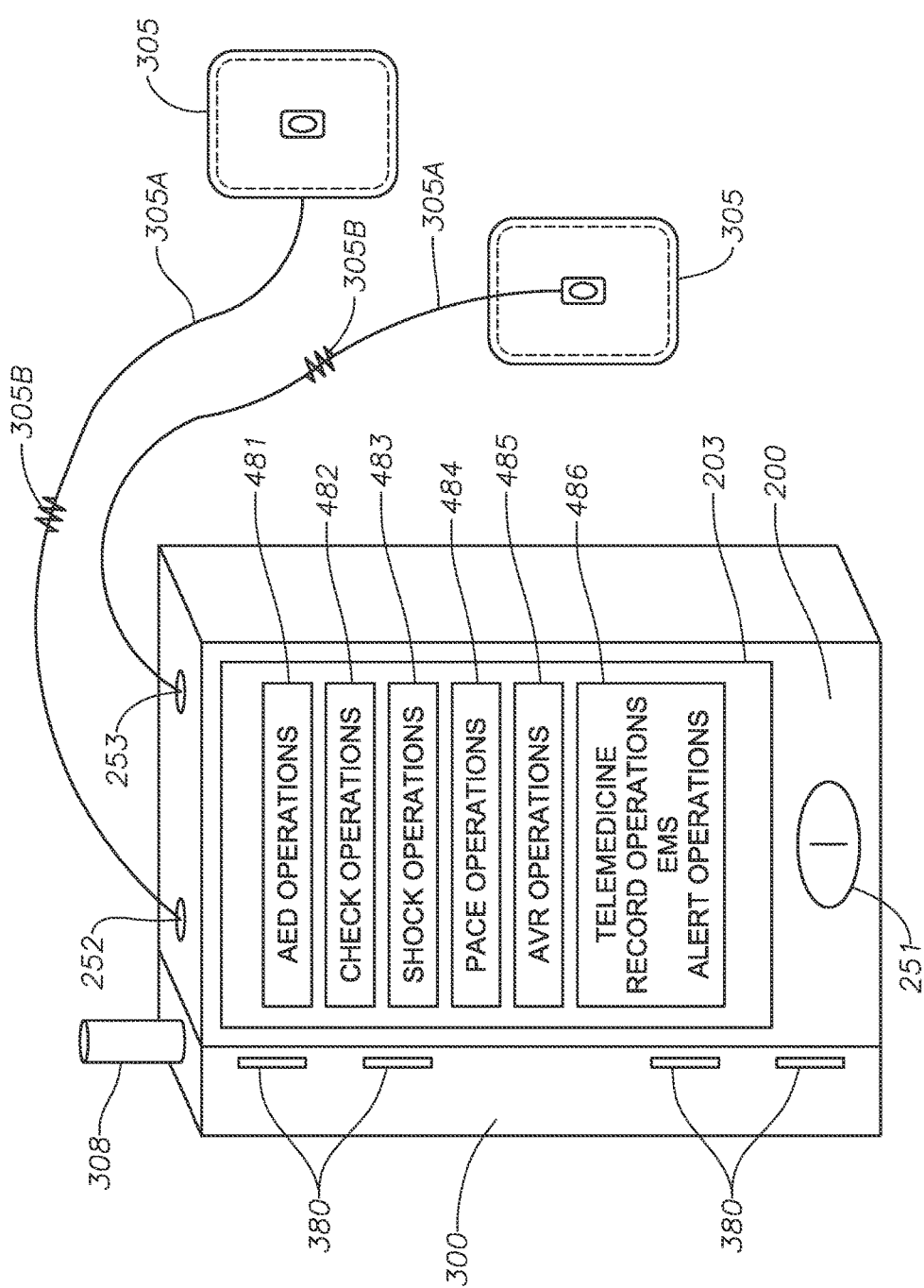
FIG. 14 is a schematic diagram of a system according to an embodiment of the invention.

For example, an exemplary system 100 is illustrated in FIG. 14. A smartphone 200 can include, for example, a display 203, a button 251, a first port 252, and a second port 253. The display 203 of the smartphone 200 can feature one or more icons associated with a user interface, such as an icon to launch AED operations 481, an icon to launch check operations 482, an icon to launch shock operations 483, an icon to launch transcutaneous pacing operations 484, an icon to launch AVR operations 485, and an icon to launch telemedicine operations 486. A protective casing 300 can include an antenna 308 and one or more charging ports 380. Charging ports 380 can provide extra charging options for the protective casing 300. The antenna 308 can provide signal transmission, boost a signal, and link to an automatic vehicle location (AVL) system, for example. Further, the protective casing 300 can include a nano-capacitor (e.g., CA123 systems/Altairenano). Extendable wires 305A of two or more extendable electrode pads 305 can include extendable portions 305B, for example. Extendable electrode pads 305 can connect to smartphone 200 through ports 252 and 253, for example.

Figure 25:
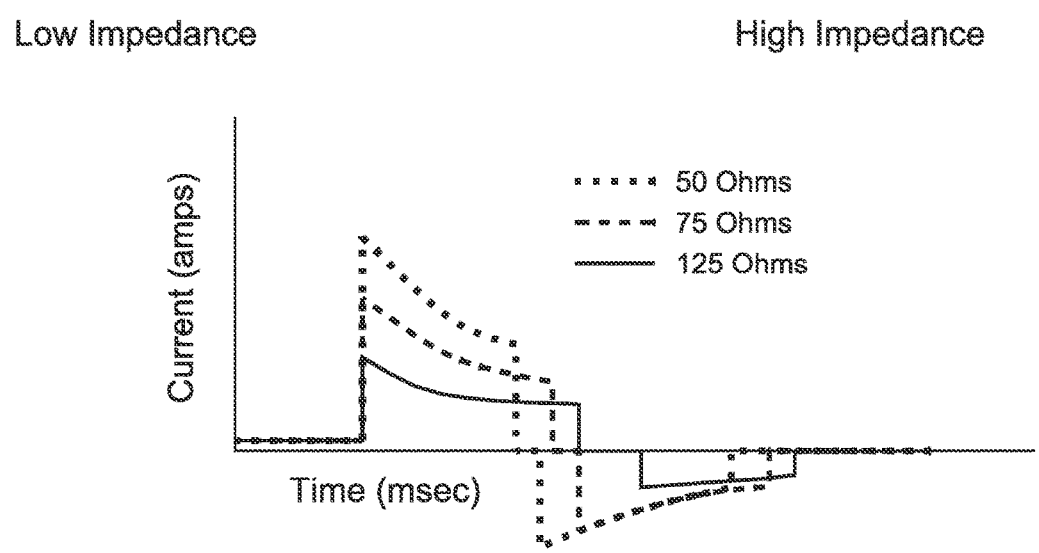
FIG. 25 is a graph of current as a function of time according to an embodiment of the invention.

In some instances, specifications of a system 100 can include a biphasic waveform that provides a shock to the heart via two vectors. That is, shocks in a system 100 can be of a biphasic type and give two sequential lower energy shocks, e.g., 120-200 joules, with each shock moving in an opposite polarity between the pads 305. Biphasic waveforms, as will be understood by those skilled in the art, can be a type of defibrillation waveform where a shock is delivered to the heart via two vectors. Biphasic waveforms were initially developed for use in implantable defibrillators and have since become a standard in external defibrillators. While all biphasic waveforms have been shown to allow termination of VF at lower current than monophasic defibrillators, two types of waveforms can be used in external defibrillators, as illustrated in FIG. 24, for example. As illustrated, electrode pads 305 can administer a shock to a victim V. The graph to the left of the victim V can illustrate one type of biphasic waveform that can be used, and the graph to the right of the victim V can illustrate another type of biphasic waveform that can be used. Each graph can illustrate current over time. In some instances, individual defibrillator manufacturers can approach biphasic defibrillation differently. For example, both Physio Control and Philips use the biphasic truncated exponential (BTE) waveform originally developed for internal defibrillators, though they use different energy settings with the waveform. Physio Control uses a "high energy" biphasic waveform (branded as ADAPTIV™ Biphasic). Physio Control energy settings go up to 360 joules of energy and can distribute the voltage and current available over a wider range of energy settings. Additionally, they vary the voltage and extend the duration of the shock in higher impedance patients. Therefore, with a Physio Control BTE waveform, differences in the waveform can occur between victims with different impedances, as illustrated in FIG. 25, for example, which depicts current over time at three impedance levels. Philips Medical also uses the BTE waveform in its SMART Biphasic device, but this device can distribute the voltage and current available over a more narrow range of energy with the maximum current delivered at 200 joules, that is, roughly equivalent to that delivered by the Physio Control device at 360 J.

Figure 26:
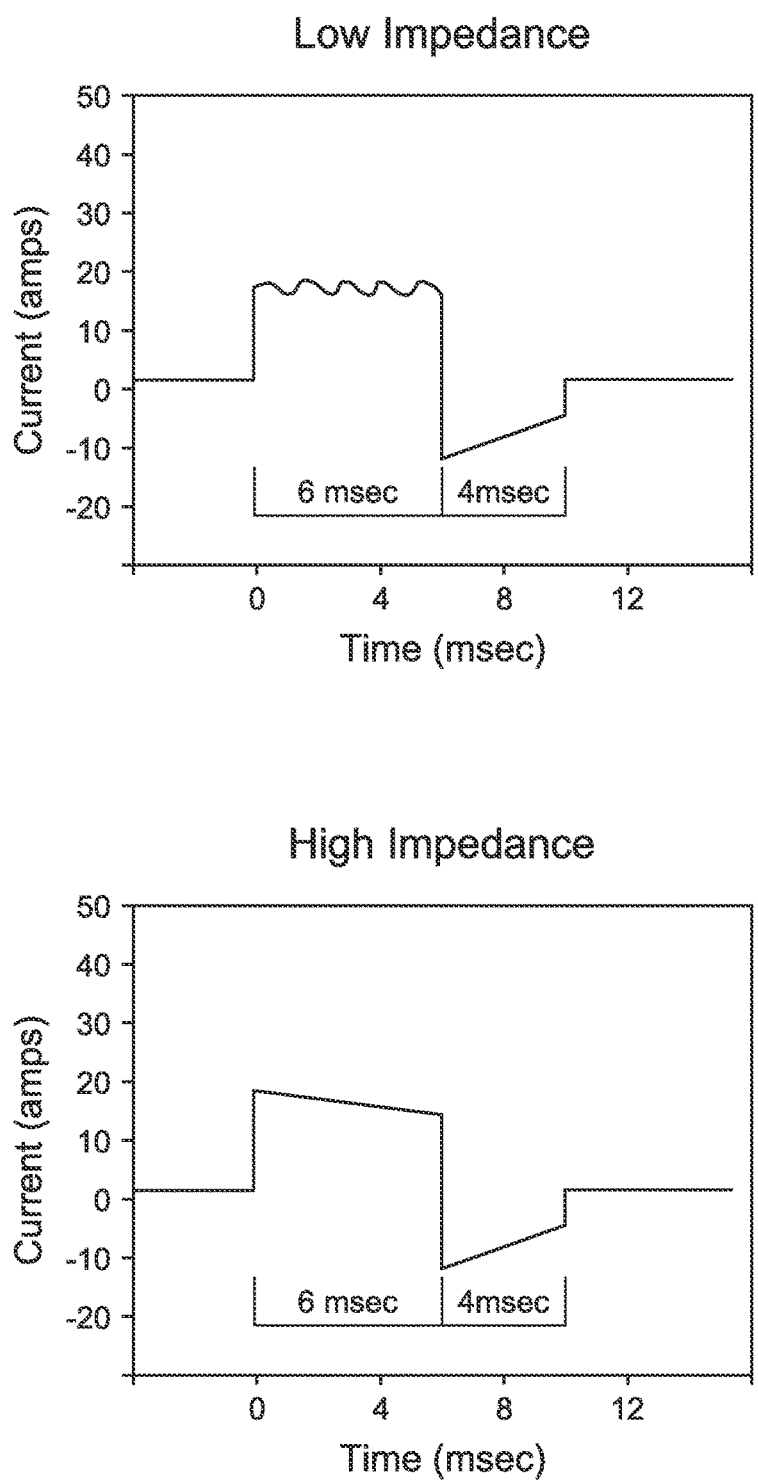
FIG. 26 is two graphs of current as a function of time according to an embodiment of the invention.

The Rectilinear Biphasic Waveform (RBW) is used by ZOLL Medical, and it differs from both of the BTE waveform devices. ZOLL fixes voltage at the maximum and varies resistance in order to deliver constant current across the broad range of victims. Similarly to Philips, 200 joules can be the maximum setting on the defibrillator; this maximum represents more voltage on the capacitor than either Physio Control or Philips has available, however. Additionally, the duration of the ZOLL RBE waveform can be fixed at 10 msec. The defibrillation threshold can decrease with increasing time up to a point around 10-12 msec, after which the defibrillation threshold can begin to increase. As there is concern in the literature about the effects of current on myocardial stunning, ZOLL chooses not to go beyond that threshold. The ZOLL RBW defibrillator actually divides impedance into two components: equipment-based impedance and patient-based impedance. Rather than adjusting the secondary variables, such as voltage and time, the ZOLL RBW adjusts the equipment-based impedance and adds or subtracts resistors in the equipment as required to control for an essentially "constant" current during the course of the first phase. For example, for a 200 J energy setting, the ZOLL RBW can charge the capacitor to the maximum voltage regardless of patient impedance. In the case of a patient with 50 ohms of impedance, the defibrillator controller can add ohms of resistance to effectively "dampen" the amount of current being delivered to the patient. For a patient with 150 ohms of impedance, equipment-based resistors can be omitted, and the full amount of current can be delivered to the patient. In laboratory bench tests, at 200 J, ZOLL delivered a 27.8 A peak current and a 24.0 A average current to a 50 ohm resistor and a 14.8 A peak current and a 12.5 A average current to a 150 ohm resistor. At energy settings less than 200 J, the difference between peak and average current can be even less, e.g., typically a maximum of 1 A. A comparison of current over time at low versus high impedance is illustrated in FIG. 26, for example.

Alternatively, such specifications of a system 100 further can include a sinusoidal waveform that provides uniphasic characteristic pulses that have a duration of 0.05 ms and can reach 1 mA. That is, shocks can be of a monophasic type and give a high-energy shock, e.g., up to 360-400 joules. Monophasic waveforms, as will be understood by those skilled in the art, can be a type of defibrillation waveform in which a shock is delivered to the heart from one vector as shown in FIG. 23, for example. As depicted, current can pass through a victim V between electrode pads 305. Further, for example, current over time in a monophasic waveform is illustrated in FIG. 23. A monophasic waveform can prevent any ability to adjust for patient impedance. Further, it is generally recommended that all monophasic defibrillators deliver 360 J of energy in adult victims to ensure that a maximum current is delivered in the face of an inability to detect patient impedance. Monophasic shocks can increase cardiac injury and chest burns around the shock pad sites as a result, however.

In some embodiments of the invention, a battery or batteries of smartphone 200 can be lithium polymer and can provide 3.7 V or 4.2 V of power. In contrast, the power provided by the battery or batteries (e.g., lithium batteries) of an AED unit can be 360 joules, which can be equivalent to 3000 V. A protective casing 300 can include an enhancer that can draw power (e.g., 3.7-4.2 V from a battery of a smartphone 200) and increase the energy discharge to reach the required energy level (e.g., 360 joules).

Embodiments of the invention advantageously can include use of nanotechnology, for example. Nanotechnology can include the engineering and manipulation of materials at the molecular level. This emerging technology can create materials with dimensions ranging from one to 100 nanometers, for instance. Further, particles created at the nanoscale can have different chemical and physical properties than larger particles of the same material. These manufactured nanoparticles can be known as engineered nanoparticles, for example, as a result of their small dimensions, larger surface area relative to size, and potential ability to penetrate cells more easily than larger particles. Bio-nanotechnology components of embodiments of the invention can include nano-coating for the electrodes or pads 305 that are stored in the phone casing 300 and one or more nano-capacitors 304 for administering the current required for defibrillation, for example.

Energy applications of nanotechnology can be very relevant in creating energy for embodiments of the invention to have enough energy to function as a defibrillator, e.g., generating enough energy to create a shock of 360 J/(1000V)<$1/1000$ sec$^{-1}$. (Current requirements can range up to 20 A and can depend on the resistance of the chest and body, and voltage can range from 1000-6000 V. Further, the time of discharge can be 5-10 ms.) The design of higher energy storing capacitors can be important to embodiments of the invention. A capacitor's capacitance (C), i.e., the amount of energy stored, is equal to the amount of charge (Q) stored on each plate divided by the voltage (V) between the plates. Additionally, capacitance (C) is approximately equal to the permittivity ($\in$) of the dielectric times the area (A) of the plates divided by the distance (d) between them. Capacitance is proportional to the surface area of the conducting plate and inversely proportional to the distance between the plates. Consequently, carbon nanotubes can be useful in embodiments of the invention because the properties of carbon nanotubes are such that they have a very high surface area to store a charge. In light of the relationship between capacitance (C) and the surface area (A) of the conducting plate, using nanoscaled materials with a high surface area can increase capacitance. The other proportionality described above is that capacitance (C) is inversely proportional to the distance (d) between the plates. Using nanoscaled plates, such as carbon nanotubes created through nanofabrication techniques, gives the capability of decreasing the space between plates, which again can increase capacitance.

An important subfield of nanotechnology related to energy can include nanofabrication. Nanofabrication is the process of designing and creating devices on the nanoscale. Creating devices smaller than 100 nanometers can open many doors for the development of new ways to capture, store, and transfer energy, for example. Nanofabrication can provide capabilities to solve many of the problems that the world is facing today related to the current generation of energy technologies. Benefits from the design of such nanofabricated products can include an increased efficiency of light and heat, for example, which can be linked to increased electrical storage capacity and a decreased amount of pollution from the use of energy. An example of utilizing nanotechnology for battery technology can include using nanomaterial to alter the wetting behavior of a surface where liquid in a battery lies. Such an alteration can allow the liquid droplets to spread over a greater area on the surface and therefore can enable greater control over the movement of the droplets, which can give more control to the designer of the battery. This control can prevent reactions in the battery by separating electrolytic liquid from the anode and cathode when the battery is not in use then joining them when the battery is required. Additionally, this control can provide the basis of the nano-capacitors for a battery used in some embodiments of the invention. Such nano-power can be self-charging, for instance. Further, a specific ultracapacitor can be used. An ultracapacitor can be a general term that describes a capacitor that contains nanocomponents, for example. Ultracapacitors features can include high density interior, compact size, reliability, and high capacitance. For example, ultracapacitors can have the capability to supplement batteries in hybrid vehicles and therefore can power and sustain hybrid vehicles by providing 2-4 Megajoules/lap around a Formula 1 track. Likewise, ultracapacitors can have enough capacity to function as a defibrillator, which can require 360-400 joules.

Carbon nanotubes can be a possible material for use in an ultracapacitor, for example. Carbon nanotubes can be created by vaporizing carbon and allowing it to condense on a surface. When the carbon condenses, it can form a nano-sized tube composed of carbon atoms. Such a tube can have a high surface area, which can increase the amount of charge that can be stored. Some non-limiting examples of options for a nano-battery according to embodiments of the invention are listed in the table in FIG. 19, for example.

An embodiment of the invention further can include a protective casing 300 to enhance use of an automated external defibrillator (AED) device before arrival of emergency medical personnel and adapted to abuttingly contact one or more side portions of and retain a mobile phone configured to communicate with the Internet thereby to define a smartphone 200 when the smartphone 200 is positioned therein. The protective casing 300 can include one or more processors thereby to define casing processors 301 and one or more input and output units 302 in communication with the casing processors 301. The one or more input and output units 302 further can be in communication with a smartphone 200. The protective casing 300 also can include one or more sensors 303 in communication with the casing processors 301 and one or more capacitors 304 in communication with the casing processors 301. The protective casing 300 further can include two or more extendable electrode pads 305 in communication with the casing processors 301 and configured to transmit a current responsive to activation of the one or more capacitors 304. Still further, the protective casing 300 can include non-transitory memory medium 306 in communication with the casing processors 301. The non-transitory memory medium 306 can be configured to include a plurality of modules 307, for example. Each of the modules 307 can include computer-readable instructions stored in the computer-readable medium 306 that when executed by the casing processors 301 cause the casing processors 301 to perform operations. For example, the modules 307 can include a check module 310 to determine, by use of the two or more extendable electrode pads 305 and the one or more sensors 303, whether the victim's heart rhythm requires an electrical shock to reestablish a normal heart rhythm responsive to input from the smartphone 200, as illustrated, for example, in FIG. 4. That is, operations of the check module 310 can include analyzing a victim's heart rhythm and determining if a shock is required to save the victim. The modules 307 also can include a space module 320 to measure, by use of the one or more sensors 303, presence and amount of preselected materials relatively near the protective casing 300 thereby to define environmental data responsive to the check module 310. For example, operations of the space module 320 can include the functionality to assess any hazards of the surrounding environment (e.g., nearness to lower explosive limit (LEL), $H_2S$ emissions, gases, inflammables, combustibles close by, etc.). The modules 307 further can include a shock module 330 to activate the one or more capacitors 304 and generate an electrical current between the two or more extendable electrode pads 305 to deliver an electrical shock to the victim's chest by use of the two or more extendable electrode pads 305 responsive to the check module 310, the space module 320, and input from the smartphone 200.

Figure 4:
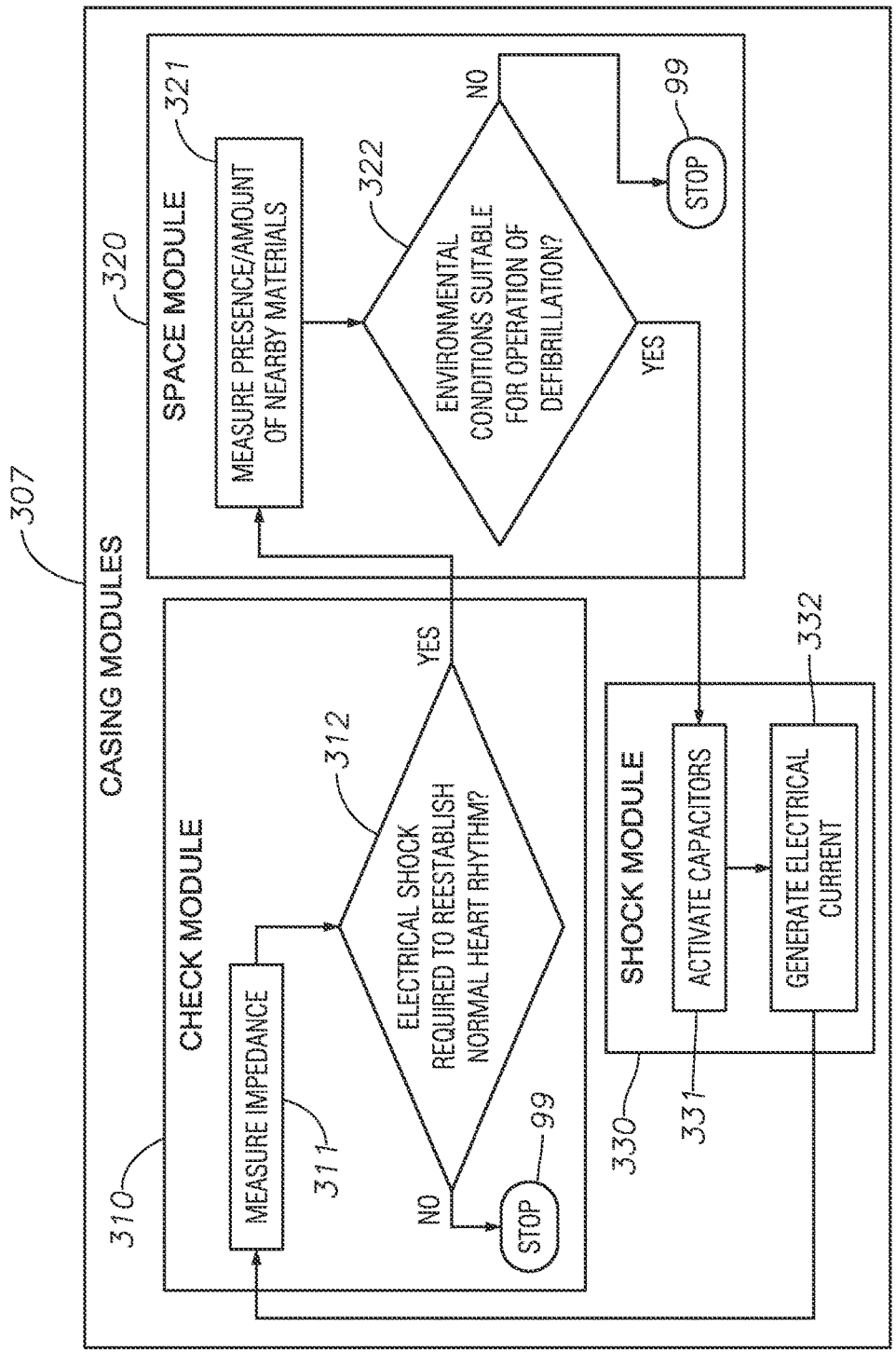
FIG. 4 is a schematic diagram of modules of a protective casing according to an embodiment of the invention.

In some circumstances, the two or more extendable electrode pads 305 can include a layer of nanomaterials on each surface of the two or more extendable electrode pads 305 adapted to be positioned on the victim thereby to define two or more extendable electrode nano-coated pads. Further, operations of the check module 310 can include measuring, by use of the two or more extendable electrode pads 305 and the one or more sensors 303, impedance of a victim's body. Operations of the check module 310 also can include determining, responsive to a determination that the victim's heart rhythm requires an electrical shock to reestablish a normal heart rhythm, an electrical shock energy level required to reestablish a normal heart rhythm to the victim's heart. For example, operations of the check module 310 can include, for example, measuring impedance 311 and determining whether an electrical shock is required to reestablish a normal heart rhythm 312, as illustrated in FIG. 4, for example. If an electrical shock is not required 312, operations can include stopping 99. If an electrical shock is required 312, however, operations of the space module 320 can begin. For example, operations of the space module 320 can include measuring presence and amount of nearby materials 321 then determining whether the environmental conditions are suitable for operation of defibrillation 322. If environmental conditions are unsuitable for operation of defibrillation 322, operations can include stopping 99. If environmental conditions are suitable for operation of defibrillation 322, however, operations of the shock module 330 can begin. For example, operations of the shock module can include activating the one or more capacitors 331 and generating an electrical current 332. After generating an electrical current 332, operations of the check module 310, e.g., measuring impedance 311, can begin again.

Additionally, in some instances, the preselected materials can include one or more of the following: oxygen, carbon monoxide, $H_2S$ emissions, gases, inflammables, and combustibles. Further, the protective casing 300 can be in communication with the smartphone 200 through a Bluetooth connection, and one or more batteries of the smartphone 200 can provide power to charge the one or more capacitors 304. The protective casing 300 further can include a direct current (DC) booster configured to amplify the power provided by the one or more batteries of the smartphone 200. In addition, the protective casing 300 further can include a compartment adapted to house the two or more extendable electrode pads 305 thereby to separate the two or more extendable electrode pads 305 from one or more other components of the protective casing 300. An exemplary embodiment of a protective casing 300 is illustrated in FIG. 13, for example. A protective casing 300 can include, for instance, a body 370. The protective casing 300 also can include a cover 371 attached to the body 370 by one or more connections, such as hinges 377. In addition, the protective casing 300 can include a partition 372 that is connected to the body by one or more connections, such as hinges 376. Advantageously, the body 370, with the partition 372 for example, can form a compartment adapted to house adhesive, paired two or more extendable electrode pads 305, including the associated wires 305A, thereby to separate the two or more extendable electrode pads 305 from one or more other components of the protective casing 300. That is, the compartment can be a portion of the body 370 of the protective casing 300, and the protective casing 300 further can include a component that has one or more substantially rectangular faces, is connected to the body 370 of the protective casing 300 by one or more connections, such as hinges 377, and is adapted to substantially enclose the compartment when in a closed position thereby to define a compartment cover 371. The compartment cover 371 can be adapted to enclose the two or more extendable electrode pads 305 when in the closed position. In some instances, a 3D printer can be used to build a protective casing 300 according to embodiments of the invention, for example.

Figure 27:
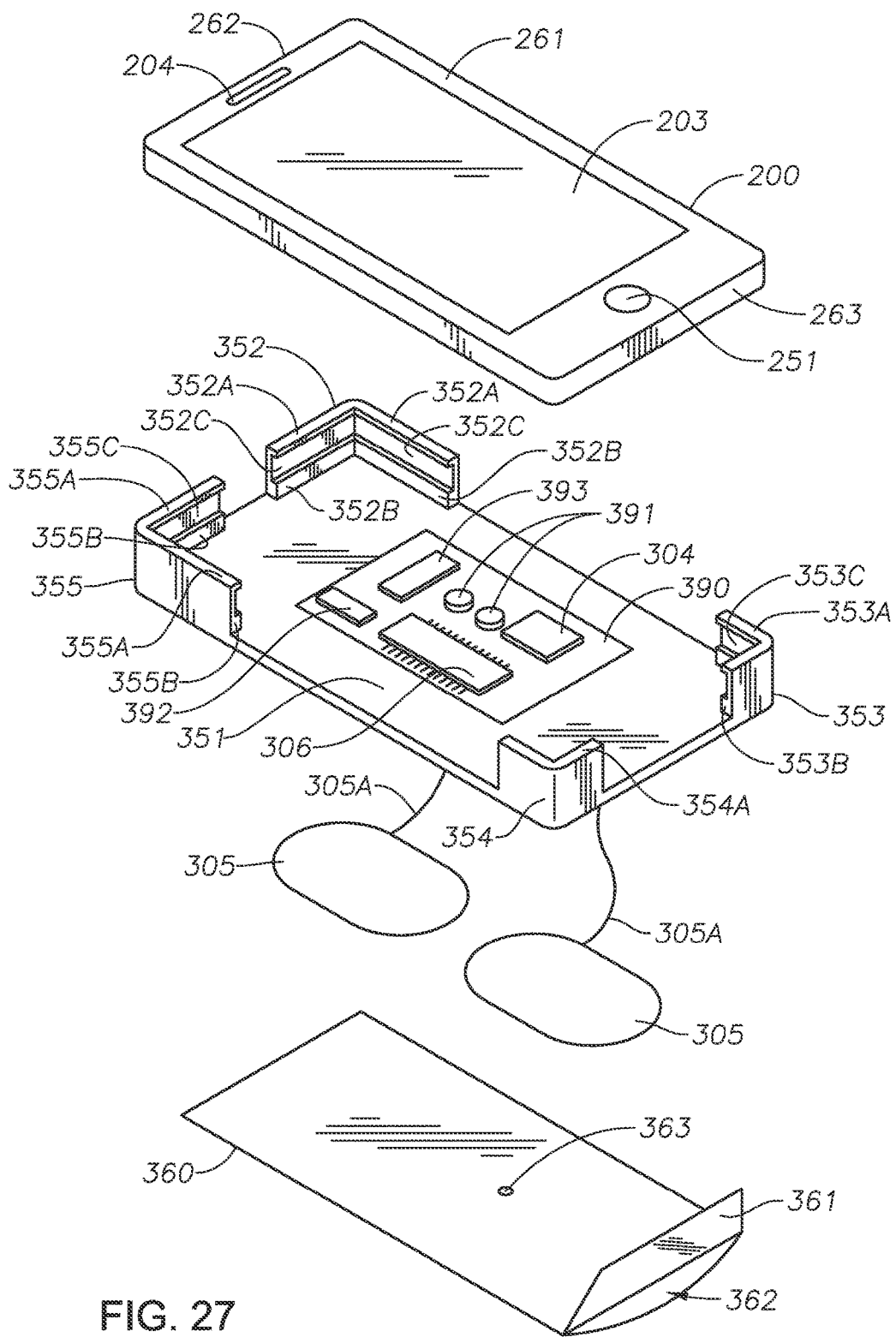
FIG. 27 is a schematic diagram of a system according to another embodiment of the invention.
Figure 28:
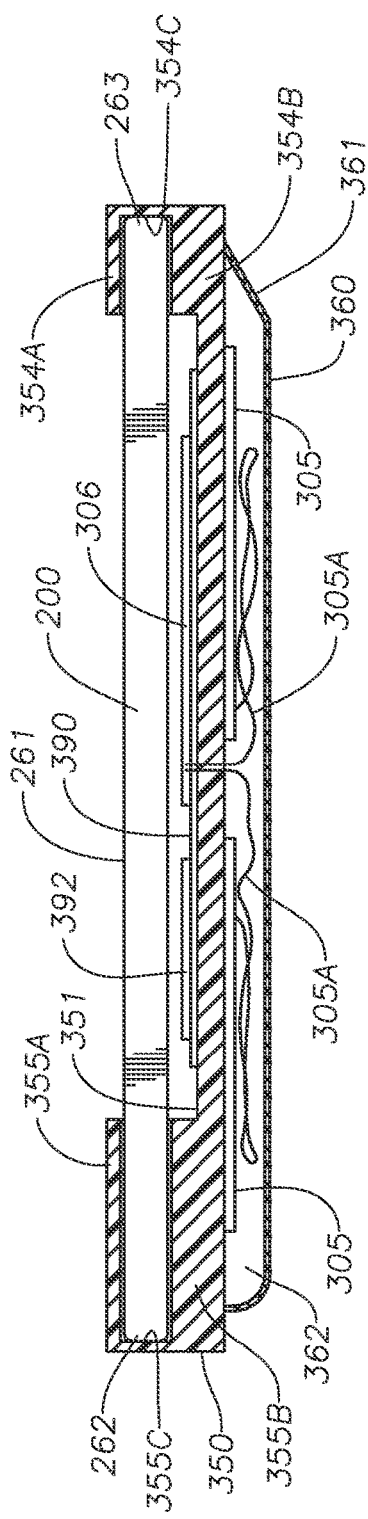
FIG. 28 is a schematic diagram of a system according to another embodiment of the invention.
Figure 29:
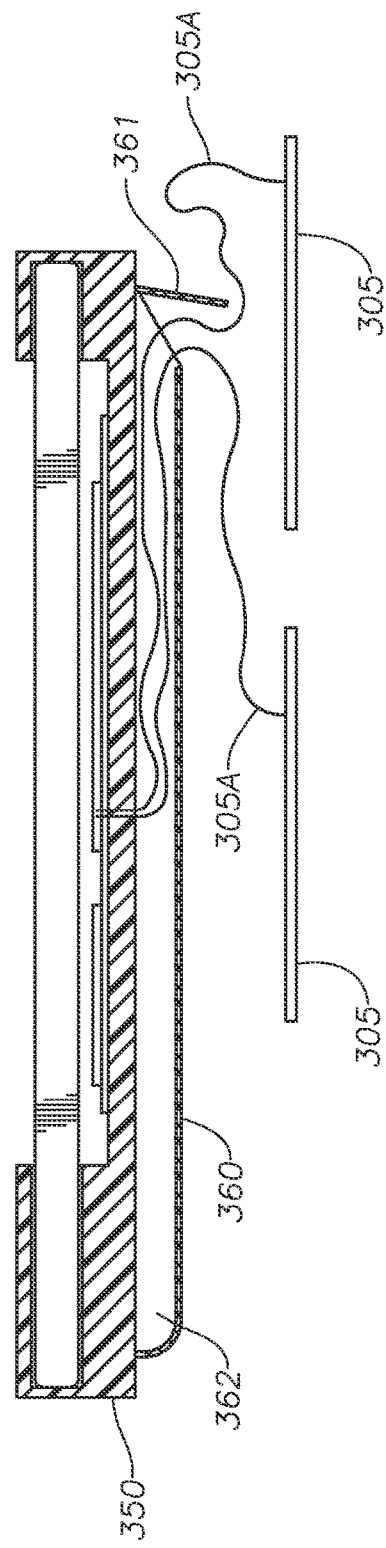
FIG. 29 is a schematic diagram of a system according to another embodiment of the invention.

Further, another exemplary embodiment of a protective casing 300 is illustrated in FIG. 27, FIG. 28, and FIG. 29, for instance. A protective casing 300, as illustrated, can include an alternative body 350 of the protective casing 300, as illustrated in FIG. 28, for example. The body 350 can include an interior face 351 adapted to be positioned adjacent a smartphone 200 when positioned therein, as illustrated in FIG. 27, for example. The body 350 also can include one or more corner support flanges, such as flange 352, flange 353, flange 354, and flange 355. Each flange can be adapted to retain a corner of a smartphone 200. For example, flange 352 can include a lower lip 352B, an upper lip 352A, and recessed medial portions 352C. When a smartphone 200 is positioned within the protective casing 300, flange 352 can abuttingly contact and retain a corner of the smartphone 200 in between the lower lip 352B and the upper lip 352A. Similarly, flange 353 can include a lower lip 353B, an upper lip 353A, and recessed medial portions 353C, and flange 355 can include a lower lip 355B, an upper lip 355A, and recessed medial portions 355C. As further illustrated in FIG. 28, for example, flange 354 likewise can include a lower lip 354B, an upper lip 354A, and recessed medial portions 354C. Additionally, flange 355 can abuttingly contact and retain side peripheries 262 of the smartphone 200 in between the lower lip 355B and the upper lip 355A such that side peripheries 262 abuttingly contact recessed medial portions 355C of flange 355, as illustrated in FIG. 28, for instance. Further, flange 354 can abuttingly contact and retain other side peripheries 263 of the smartphone 200 in between the lower lip 354B and the upper lip 354A such that side peripheries 263 abuttingly contact recessed medial portions 354C of flange 354. Advantageously, a face 261 of the smartphone 200 can remain visible and accessible to a user when the smartphone 200 is positioned within the protective casing 300, as illustrated in FIG. 28, for example. The protective casing 300 further can include a microcontroller board 390 positioned adjacent the interior face 351, as illustrated in FIG. 27, for example. The microcontroller board 390 can include one or more memories 306, one or more capacitors 304, one or more batteries 391, and one or more input/output ports, such as input/output port 392 and input/output port 393. The microcontroller board 390 may use any of input/output units 302, 392, 393 to connect to smartphone 200 input/output unit 202 when smartphone 200 is positioned in the protective casing 300 or body 350. The protective casing 300 also can include a sleeve 360 adapted to enclose and retain the electrode pads 305 when positioned therein. The sleeve 360 can be formed to include a compartment interior 362 and a flap 361 that, when in a closed position, can enclose the compartment interior 362 and prevent items from entering or exiting the compartment interior 362. The sleeve also can include a small hole 363 through which wires 305A can connect the body 350 to the electrode pads 305, as illustrated in FIG. 28 and FIG. 29, for example. When not in use, the electrode pads 305 can be positioned within the compartment interior 362 for storage with the flap 361 in the closed position, as illustrated in FIG. 28, for instance. When the electrode pads 305 need to be used, however, the flap 361 can be opened, and the wires 305A can extend such that the electrode pads 305 are positioned outside of the compartment interior 362, as illustrated in FIG. 29, for example.

In some circumstances, the plurality of casing modules 307 further can include: (1) a sync module to generate an electrical current between the two or more extendable electrode pads 305 in a synchronized cardio version, (2) a pace module to transcutaneously pace the victim by use of the two or more extendable electrode pads 305, and (3) a self-regulation module to determine when one or more components of the protective casing 300 require replacement thereby to enable the protective casing 300 to self-regulate. In addition, the protective casing 300 can be adapted to snap the smartphone 200 into a locked position when the smartphone 200 is positioned in the protective casing 300, and the protective casing 300 can be adapted to comply with OSHA standards. The protective casing 300 also can include an inner cavity that has five or more sides, and each of the five or more sides can be adapted to contact abuttingly one or more side portions of the smartphone 200 when the smartphone 200 is in the locked position. Further, in some instances, the protective casing 300 can comply with electronic compliant "limits" for sensitive environments, e.g., nuclear plants, refineries, etc.

A method to assemble a system 100 to enhance use of an automated external defibrillator (AED) device before arrival of emergency medical personnel according to an embodiment can include positioning a mobile phone configured to communicate with the Internet thereby to define a smartphone 200 in a protective casing 300 adapted to abuttingly contact one or more side portions of the smartphone 200 and retain the smartphone 200. The protective casing 300 can be configured to include one or more sensors 303, one or more capacitors 304, and two or more extendable electrode pads 305 configured to transmit a current responsive to activation of the one or more capacitors 304. Further, an embodiment of the invention can include a method to use a protective casing 300 for a mobile phone configured to communicate with the Internet thereby to define a smartphone 200 to enhance use of an automated external defibrillator (AED) device before arrival of emergency medical personnel. For example, the protective casing 300 can be positioned to abuttingly contact one or more side portions of a smartphone 200 and retain the smartphone 200. The protective casing 300 can be configured to include one or more sensors 303, one or more capacitors 304, and two or more extendable electrode pads 305 configured to transmit a current responsive to activation of the one or more capacitors 304, for example. The method can include positioning the two or more extendable electrode pads on a victim's chest. The method then can include determining, by use of the two or more extendable electrode pads 305 and the one or more sensors 303, whether the victim's heart rhythm requires an electrical shock to reestablish a normal heart rhythm responsive to input from the smartphone 200. The method also can include measuring, by use of the one or more sensors 303, presence and amount of preselected materials relatively near the protective casing 300 thereby to define environmental data responsive to determination of whether the victim's heart rhythm requires an electrical shock to reestablish a normal heart rhythm. Further, the method can include activating the one or more capacitors 304 responsive to measurement of presence and amount of the preselected materials relatively near the protective casing 300. The method still further can include generating an electrical current between the two or more extendable electrode pads 305 to deliver an electrical shock to the victim's chest by use of the two or more extendable electrode pads 305 responsive to activation of the one or more capacitors 304.

Figure 12:
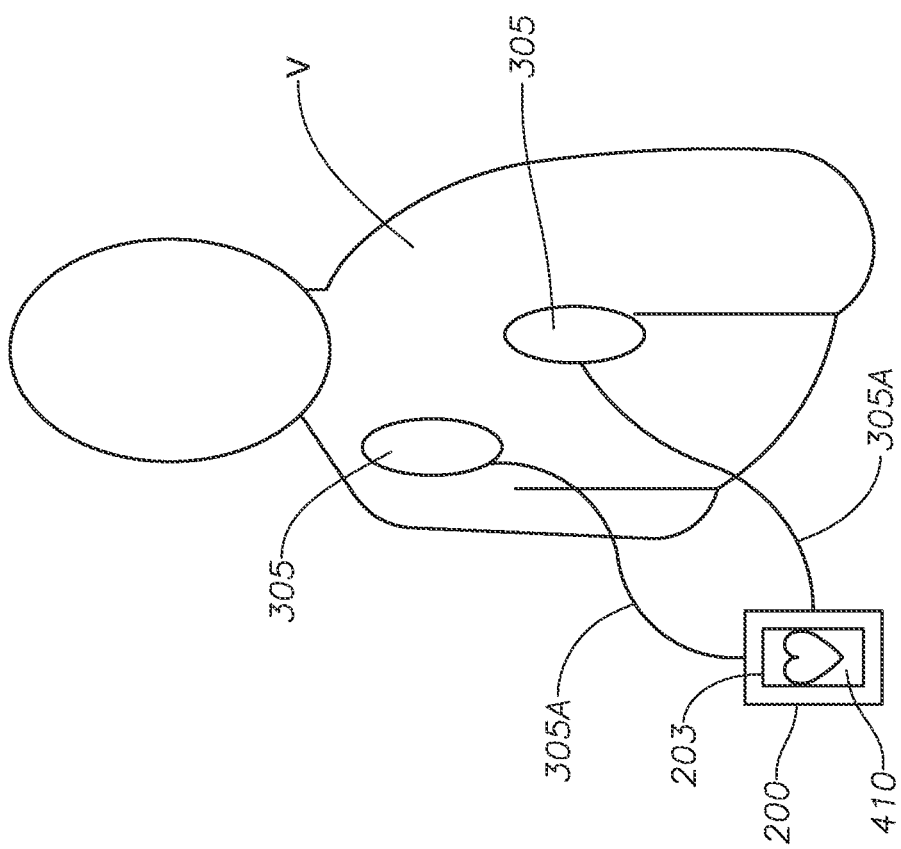
FIG. 12 is a schematic diagram of a system according to an embodiment of the invention.

For example, the two or more extendable electrode pads 305 can be placed on a victim V's chest as illustrated in FIG. 12, for instance. The extendable wires 305A of the electrode pads 305 can connect to a protective case 300 of a smartphone 200, for example. A screen 203 can display a user interface, e.g., a control interface 410. After applying the pads 305, an application can check the victim V and provide voice prompts by, e.g., a rescue coach ("Shock required: stand clear.") Further, prompts can be provided on a screen 203, e.g., in noisy embodiments, and AVR operations can scan the victim V and provide prompts and hints. All diagnostics can be recorded and transmitted directly to EMS. In addition, GPS operations can notify EMS of the location, diagnosis, real-time monitoring via signals (e.g., telecommunications). After a shock has been administered, a rescue coach can provide further instructions (e.g., "Shock administered. Start CPR.").

Figure 11:
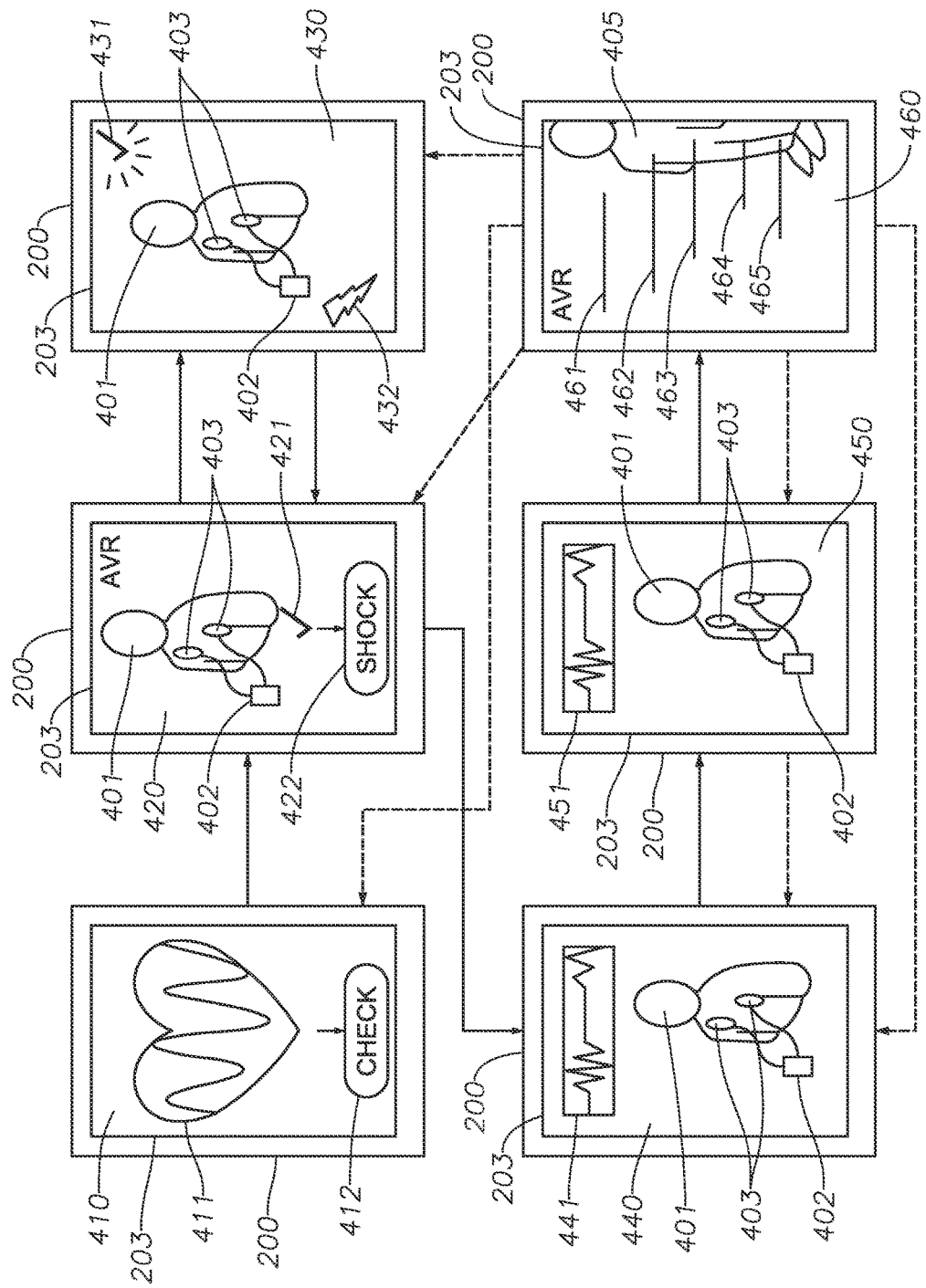
FIG. 11 is a schematic diagram of a user interface according to an embodiment of the invention.

Interfaces of a smartphone application according to an embodiment, for example, are illustrated in FIG. 11. Each interface can be displayed on a display 203 of a smartphone 200. For example, a control interface 410 can include a GIS pulse point icon 411 and a button to initiate check operations 412. Selection of check button 412 can cause a check interface 420 to be generated. A check interface 420 can include a representation of a victim 401, a representation of a smartphone and protective casing 402, and a representation of electrodes 403. In addition, a check interface 420 can include a check icon to indicate that defibrillation is indicated 421 and a button to initiate shock operations 422. Selection of a shock button 422 can cause a shock interface 430 to be generated. A shock interface 430 can include a check icon to indicate that defibrillation is indicated and in progress 431, as well as a shock icon to indicate that a shock is in progress 432. After defibrillation is complete, a check interface 420 again can be generated, followed by a pace interface 440, a sync interface 450, and an AVR interface 460. A pace interface 440 can include, for example, a transcutaneous pacing heart rate graph 441, and a sync interface 450 can include a synchronized cardioversion heart rate graph 451. Further, an AVR interface 460 can include a second representation of a victim 405, in addition to AVR scanning features at locations 461, 462, 463, 464, and 465, which can be used for diagnostic information. The lines depicted between the various illustrated interfaces in FIG. 11, for example, can indicate the sequence of the interfaces, and the broken lines can indicate sequences that depend on the relevant circumstances.

An embodiment of the invention can include an effective and efficient system that can save lives systematically without having to install static AED machines, track and monitor SCA incidents that are happening anywhere globally, and collate fatalities that were averted for management dashboards. Advantageously, embodiments of the invention can provide a solution to assist in the protection of diverse and remote workforces, for example, and can include an evidence-based lifesaving technology that can be applied by anyone who can use a mobile phone. A system according to an embodiment can include a functioning mobile phone with hardware to enable AED capabilities that has accessories, applications, training solutions, and monitoring with GIS/GPS. In some circumstances, accessories can allow for any mobile phone to be converted into a system according to an embodiment of the invention and can be sold separately. Because each AED can cost $2,000 to $5,000, embodiments of the invention advantageously can be a fraction of the cost of an AED when mass produced, for example. Further, embodiments of the invention can be integrated with sophisticated technologies and can be traceable and small enough to be in a pocket, for example, in contrast with existing available AEDs. Advantageously, embodiments of the invention can include an enhanced life-saving device that can be carried in a pocket, a bag, or a car and that can be user friendly and require minimal training.

Figure 16:
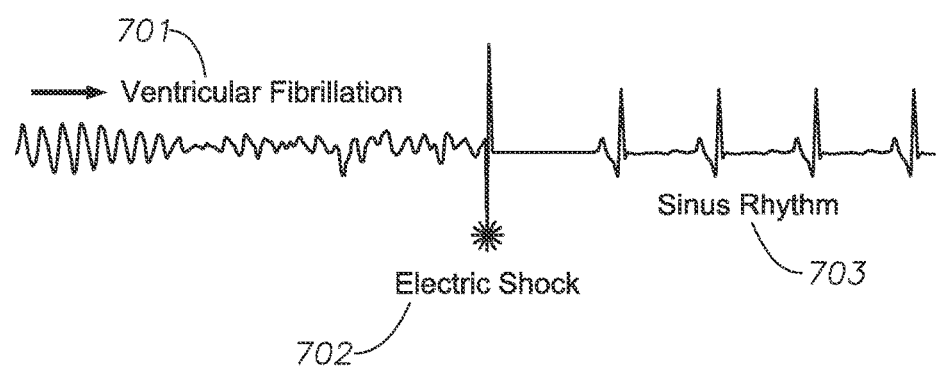
FIG. 16 is a graph of heart rhythm according to an embodiment of the invention.

A method according to an embodiment of the invention can include taking an EKG of the victim's heart to analyze the electrical activity in an attempt to determine if the victim is in VF or another heart rhythm. If the analysis indicates VF, a shock can be indicated and can be delivered by the rescuer according to operating instructions. Further, operations of a shock application, e.g., associated with a shock module 330, can include ignition of a nano-capacitor 304 and administration of a shock that has been analyzed based on the electrical needs of the individual case, as required. In addition, voice instructions can guide a user in saving the victim's life. Variable escalating energy can be monitored and measured through operations of a check application, e.g., an application associated with a check module 310. For example, operations can include determining the electrical impedance (resistance level) of each victim and customizing the energy level delivered. If more than one shock is necessary, a biphasic monitoring application can escalate the energy to deliver therapy at an appropriate, higher level, e.g., for transcutaneous pacing operations or synchronized cardioversion operations. Further, any specific medical and advanced diagnostics needs can be prompted by operations of the check application, for example. Additionally, embodiments of the invention can provide a form of telemedicine controlled by GPS mapping of the protective casing 300, e.g., to further deliver lifesaving modalities through synchronized cardioversion operations and transcutaneous pacing operations. If an end user is unsure of any steps in the methodology, there can be a chance to utilize an application for specific prompts, resources, and suggestions across all applications. Advantageously, an electric shock 702 can stop VF 701 to restore sinus rhythm 703, as illustrated in FIG. 16, for example.

Figure 17:
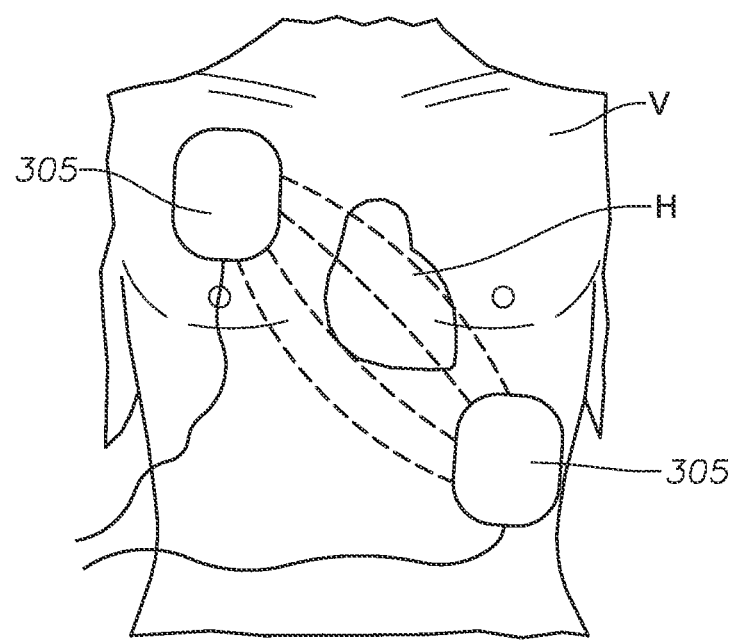
FIG. 17 is a schematic diagram of a system according to an embodiment of the invention.

Throughout an incident—from start to finish—all biometrics, data, and diagnostics can be recorded and automatically transcribed into medical notes, for example. A recording application (e.g., associated with a record module 225) can record, through biometrics and voice recognition, the status of a victim from the time of discovery to a time of when emergency services responders arrive. From the record application, all information that has been collated and recorded then can be transcribed into medical notes through a note application (e.g., associated with a note module 230), for example. Embodiments of the invention can advise a user not to touch a victim during analysis of the victim's heart and again if a shock is indicated. If the victim is touched or moved during analysis, embodiments can interrupt those movements, which can cause a potential false positive for VF, and can repeat check operations. If a shock is indicated and delivered, the heart can take up to 10 minutes to recover from the cardiac arrest. Therefore, immediately after delivering a shock (or a "no shock" indication), rescuers can resume CPR with compressions to help mechanically get the heart beating again. The check application can analyze the victim's heart rhythm and determine if a shock is required to save the victim. The shock application can provide the ignition of the nano-capacitor 304 and administer a shock (analyzed based on the electrical needs of the individual case). The extendable electrode nano-coated pads 305 can be positioned to go around the heart H of a victim V and can be placed on the upper right side of the chest below the collar bone and on the lower left side below the nipple line near the armpit, as illustrated in FIG. 17, for example. The electricity delivered then can travel in both directions between these two pads 305.

Figure 5:
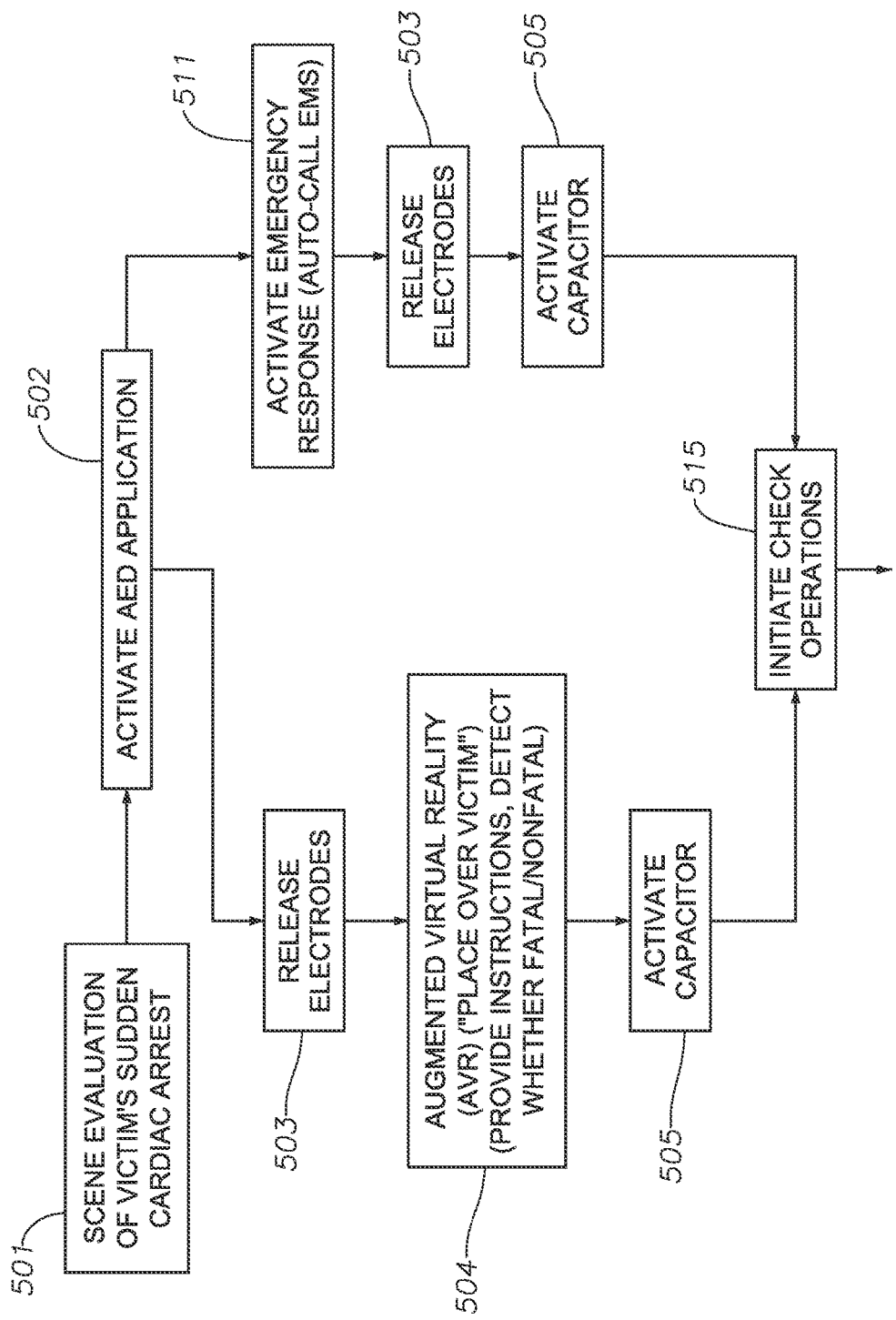
FIG. 5 is a schematic diagram of a method according to an embodiment of the invention.
Figure 6:
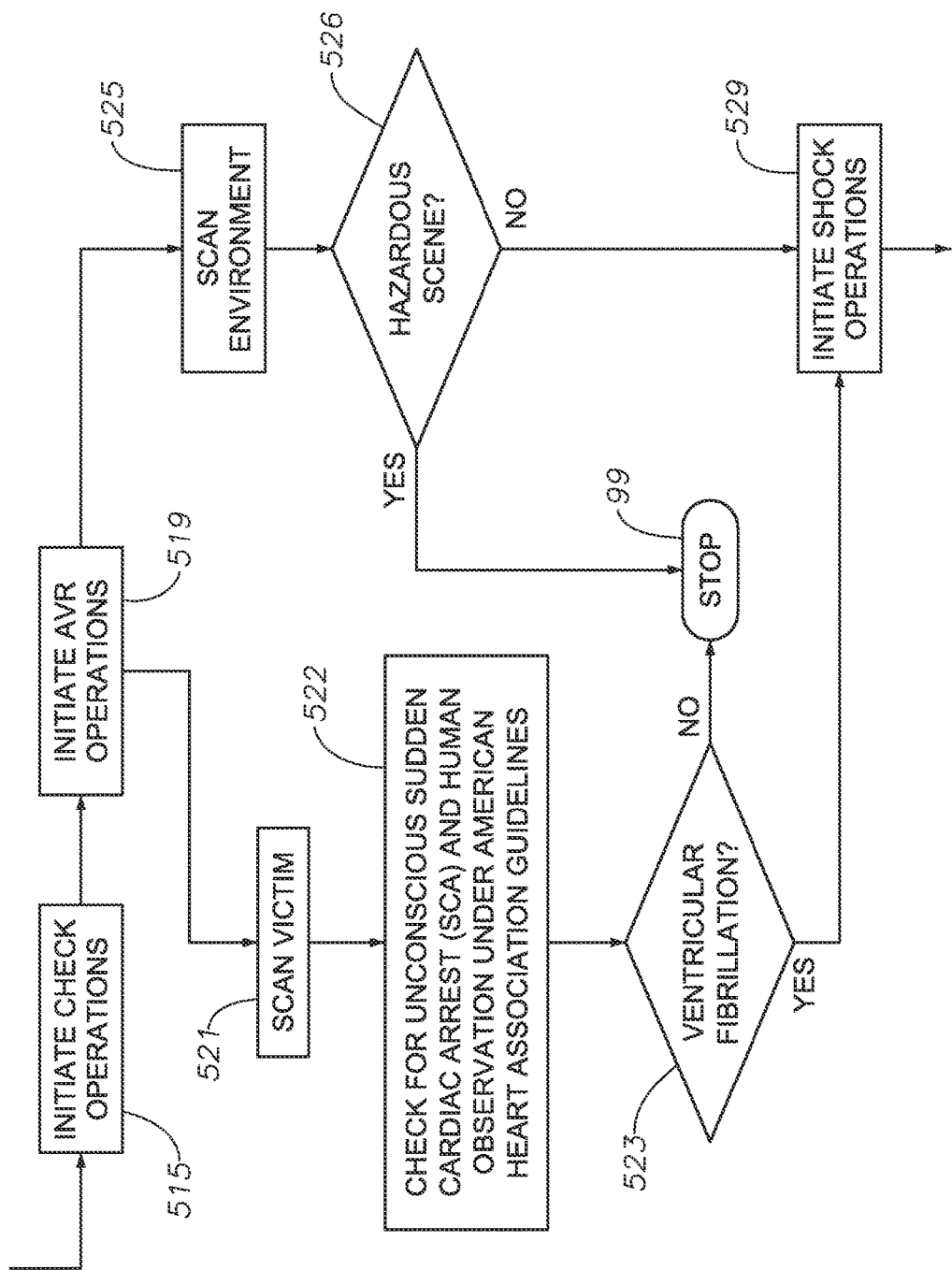
FIG. 6 is a schematic diagram of a method according to an embodiment of the invention.
Figure 7:
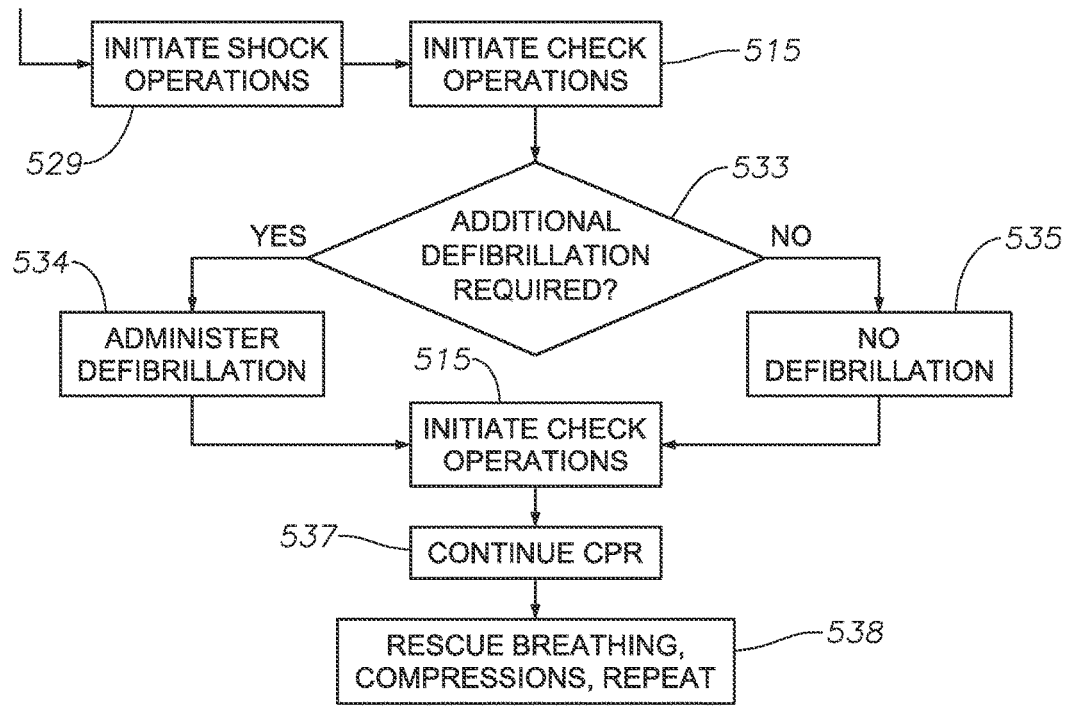
FIG. 7 is a schematic diagram of a method according to an embodiment of the invention.
Figure 8:
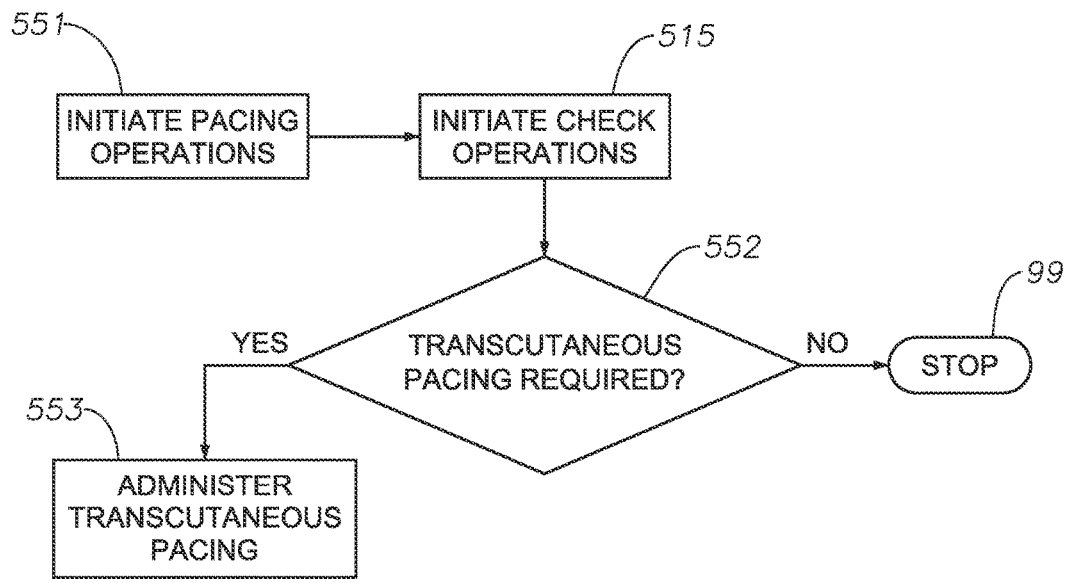
FIG. 8 is a schematic diagram of a method according to an embodiment of the invention.
Figure 9:
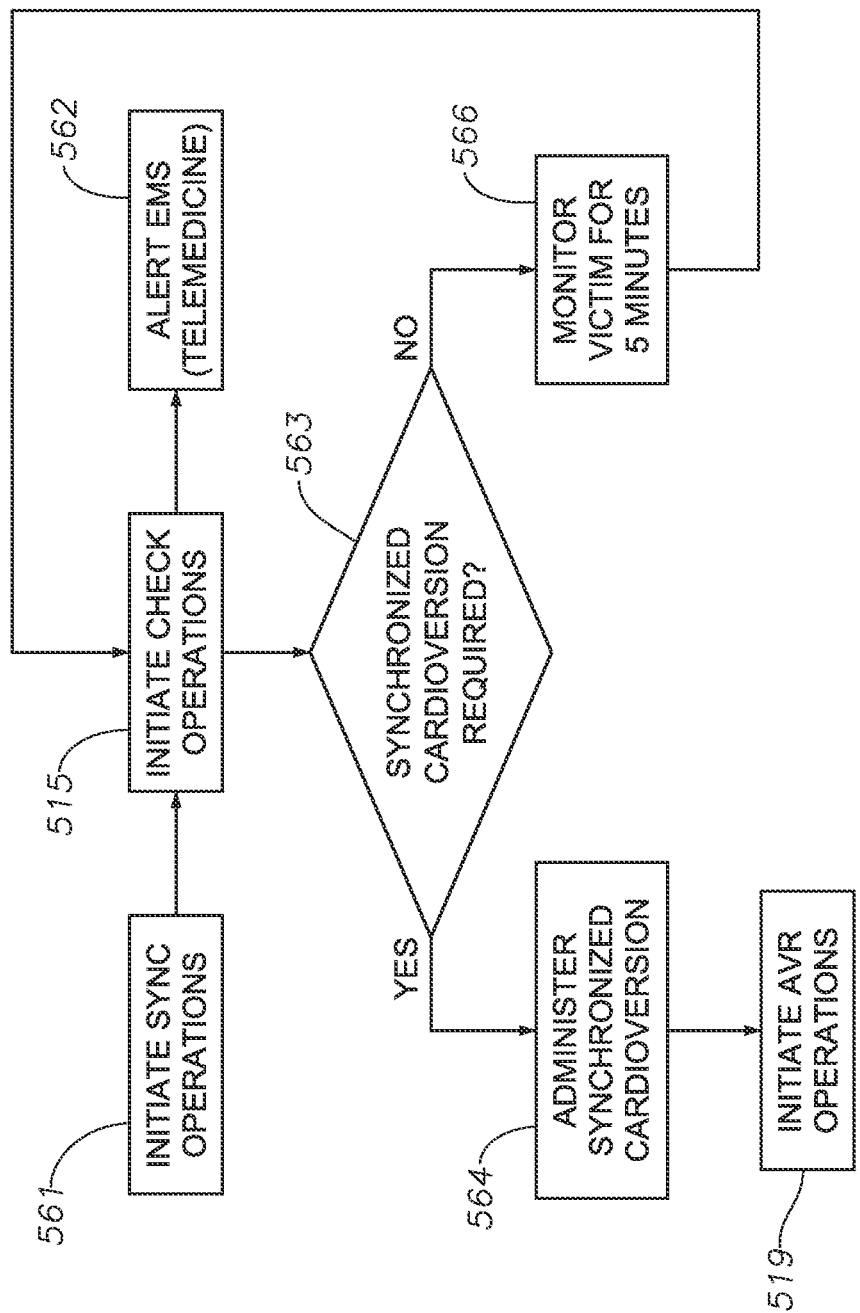
FIG. 9 is a schematic diagram of a method according to an embodiment of the invention.
Figure 10:
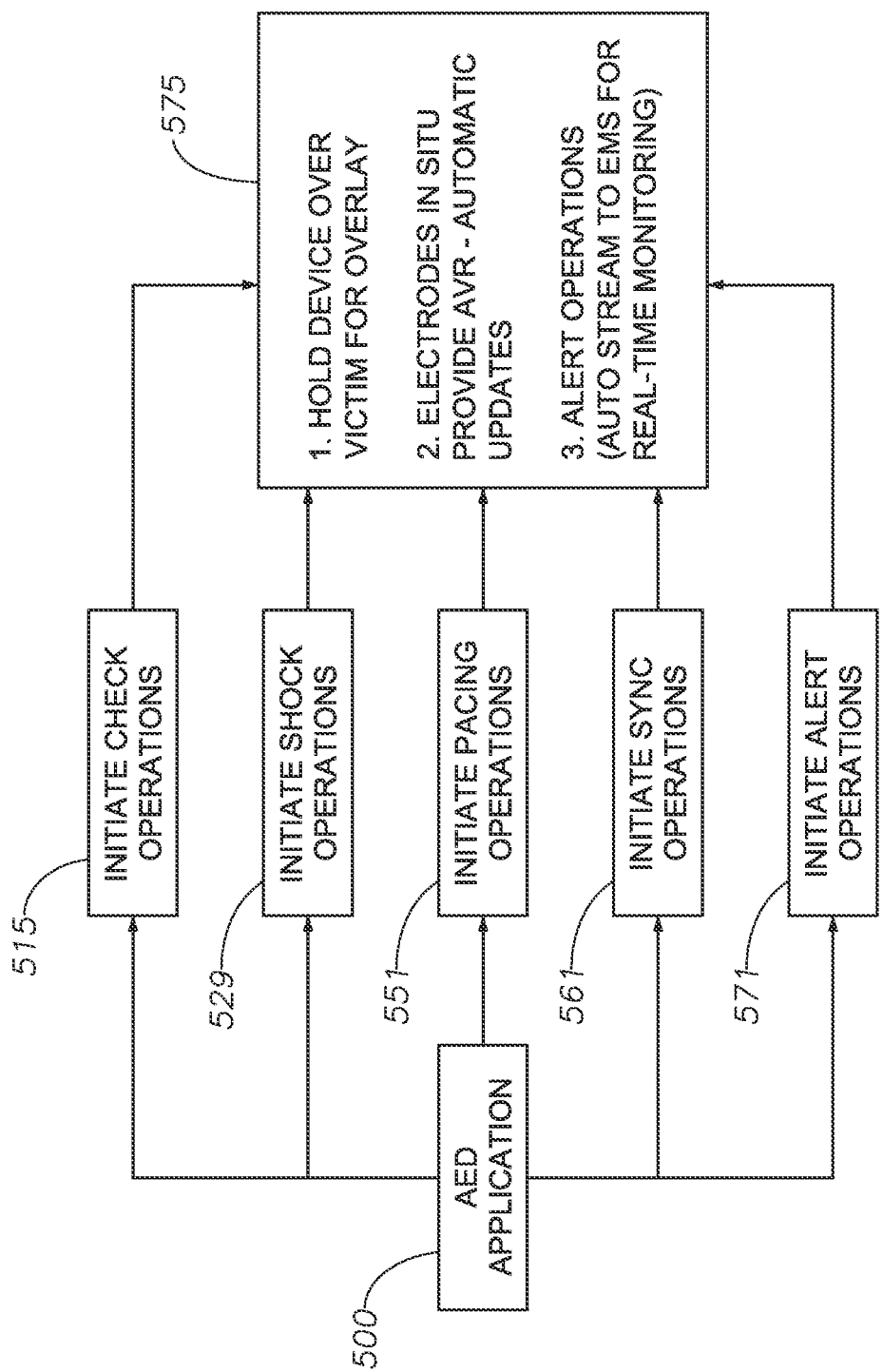
FIG. 10 is a schematic diagram of a method according to an embodiment of the invention.

For example, a method according to an embodiment of the invention is illustrated in FIGS. 5-10. Steps can include evaluating the scene of a victim's SCA 501 then activating an AED application 502, as illustrated in FIG. 5, for instance. Steps then can include releasing electrodes 503, initiating AVR operations to provide instructions and determine whether the SCA is fatal 504, activating a capacitor 505, and initiating check operations 515. In addition, steps can include activating emergency responses (e.g., auto-calling EMS) 511, releasing electrodes 503, and activating a capacitor 505 before initiating check operations 515. After initiating check operations 515, steps can include initiating AVR operations 519, as illustrated in FIG. 6, for example. Steps then can include scanning the victim 521, checking for unconscious SCA and performing human observation under the American Heart Association (AHA) guidelines 522, and determining whether ventricular fibrillation is present 523. If there is not ventricular fibrillation 523, the method can include stopping 99. If ventricular fibrillation is present 523, steps can include initiating shock operations 529. Steps also can include scanning the environment near the victim 525 then determining whether the scene is hazardous 526. If the scene is hazardous 526, the method can stop 99. If the scene is not hazardous, however, steps can include initiating shock operations 529 then initiating check operations 515, as illustrated in FIG. 7, for example. After initiating check operations 515, steps can include determining whether additional defibrillation is required 533. If additional defibrillation is not required 533, the method can include not performing an additional defibrillation 535 then initiating check operations 515. If additional defibrillation is required 533, steps can include administering defibrillation 534 then initiating check operations 515. Steps then can include continuing CPR 537, including rescue breathing, compressions, and repeating 538. Steps of the method also can relate to transcutaneous pacing, as illustrated, for example, in FIG. 8. For instance, steps can include initiating pacing operations 551, initiating check operations 515, and determining whether transcutaneous pacing is required 552. If transcutaneous pacing is not required 552, the method can stop 99. If transcutaneous pacing is required 552, steps can include administering transcutaneous pacing 553. Steps of the method also can relate to synchronized cardioversion, as illustrated, for example, in FIG. 9. For instance, steps can include initiating sync operations 561, initiating check operations 515, alerting EMS (e.g., telemedicine) 562, and determining whether synchronized cardioversion is required 563. If synchronized cardioversion is not required 563, the method can include monitoring the victim for 5 minutes 566 then again initiating check operations 515. If synchronized cardioversion is required 563, however, steps can include administering synchronized cardioversion 564 and initiating AVR operations 519. Consequently, operations of an AED application 500 of a smartphone 200 can include initiating check operations 515, initiating shock operations 529, initiating pacing operations 551, initiating sync operations 561, and initiating alert operations 571, each of which can test requisite knowledge, as illustrated, for example, in FIG. 10. As a result, a user can be directed to hold the device over the victim, place the electrodes on the victim's body, and alert EMS with real-time monitoring 575. In some instances, an emergency communication department can direct or authorize a user to perform some or all of these operations.

An AED according to an embodiment can be easy for non-medical people to use, technically reliable, and reasonably priced, similarly to Defibtech AEDs, for example. The effectiveness of a shock administered according to embodiments of the invention can be affected greatly by how well CPR is performed immediately thereafter, e.g., by doing five sets of two minutes of CPR beginning with chest compressions. In some instances, instructions can be provided exactly every two minutes. When a shock is delivered, a victim can sometimes convulse. Further, an arc of electricity sometimes can travel across the victim's body, burning hair or skin sometimes can be smelled, and smoke sometimes can be seen. However, the user can continue with CPR and use as indicated. Guidance can include direction not to remove the electrode pads 305 from the victim's chest and not to turn the device off until instructed to by trained healthcare professionals, for example. If the victim wakes up or recovers, the victim can suffer from VF again and require additional treatment.

Figure 18:
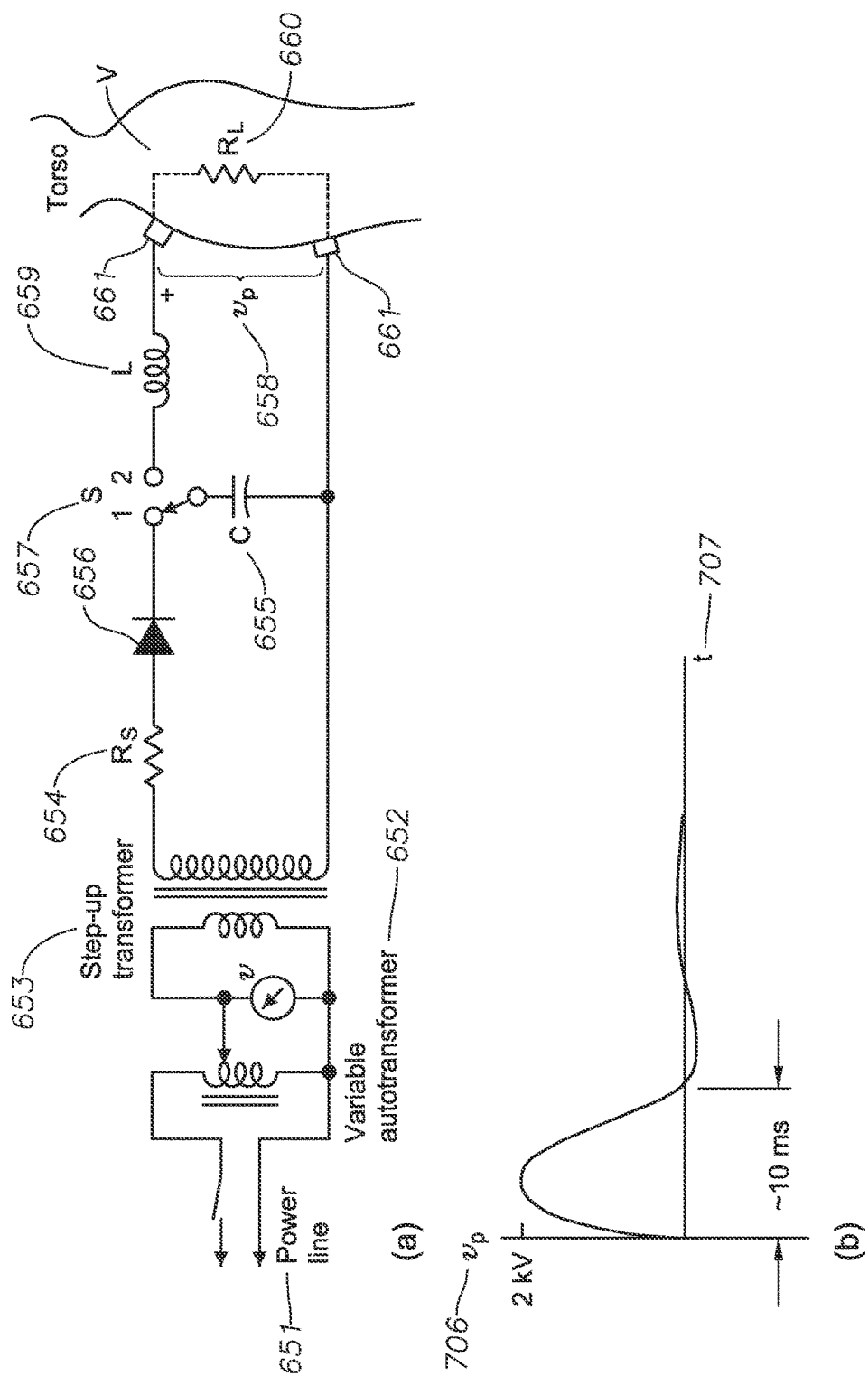
FIG. 18 is a schematic diagram of a system and associated graph according to an embodiment of the invention.

An example of some of the components of a system 100 according to an embodiment of the invention is illustrated in FIG. 15, for example. For example, an exemplary system 100 can include a smartphone 200, a DC booster 620, a circuit board 610, and two or more electrodes 615. (A protective casing 300 can include a DC booster 620 and a circuit board 610, and electrodes 615 can be two or more electrode nano-coated pads 305.) Such a system 100 can produce 360 J using a power source that provides only 5 V, such as a smartphone battery. Another example of some of the components of a system 100 according to an embodiment is illustrated in FIG. 18, for example. A system 100 can include a power line 651, a variable autotransformer 652, a step-up transformer 653, a resistor $R_s$ 654, a capacitor C 655, a diode 656, a switch 657, and an inductor L 659, as depicted in FIG. 18($a$), for instance. The victim V's torso can have a resistance $R_L$ 660, and a voltage $v_p$ 658 can exist between two electrodes 661. Further, voltage 706 over time 707 is illustrated in the graph in FIG. 18($b$), for example.

In some instances, an embodiment of the invention can feature a design similar to a stun gun because the internal structure of a stun gun and basic TASER can assist as a design model for a mobile phone device that is more compact compared to a traditional external defibrillator. The electricity delivered by an AED during a shock can stun the heart in an attempt to stop the abnormal rhythm, and an AED can operate similarly to a TASER for the heart by temporarily stunning the heart, stopping what the heart is doing, and allowing it to potentially recover. A stun gun can have a fairly simple design. Further, a stun gun can be about the size of a flashlight and can work using an ordinary 9-volt battery. One or more batteries can supply electricity to a circuit consisting of various electrical components. The circuitry can include multiple transformers, e.g., specific components that can boost the voltage in the circuit, typically to between 20,000 and 150,000 volts, and reduce the amperage. The circuitry also can include an oscillator, a component that can fluctuate a current to produce a specific pulse pattern of electricity. This current then can charge a capacitor. A capacitor can build up a charge and release it to the electrodes, i.e., the "business end" of the circuit. The electrodes can simply be two plates of conducting metal positioned in the circuit with a gap between them. Since the electrodes can be positioned along the circuit, they can have a high voltage difference between them. If this gap is filled with a conductor (e.g., an unconscious victim), the electrical pulses can try to move from one electrode the other, dumping electricity into the attacker's nervous system. In addition, a stun gun can have two pairs of electrodes: an inner pair and an outer pair. The outer pair, the charge electrodes, can be spaced a good distance apart such that current can only flow if an outside conductor is inserted. If the current cannot flow across these electrodes, it can flow to the inner pair, i.e., the test electrodes. These test electrodes can be close enough that the electric current can leap between them. The moving current can ionize air particles in the gap and thus produce a visible spark and crackling noise. This display can be mainly intended as a deterrent, in some cases. For example, an attacker can see and hear the electricity and can know that the stun gun user is armed. However, a stun gun sometimes can rely on the element of surprise rather than warning, e.g., a model disguised as an umbrella, flashlight, or other everyday object, thereby to catch an attacker off guard. Such a stun gun can be small, easy to use, and legal in most areas. Police and military forces, on the other hand, can use more complex stun gun designs with larger ranges, for example.

For instance, an example of components of a stun gun 670 is illustrated in FIG. 21. A stun gun 670 can include, for instance, a voltage amplifier circuit 671, a battery compartment 672, a trigger 673, charge electrodes 679, test electrodes 678, electrode projectiles 676, and additional electrodes 677. A stun gun 670 also can include a compressed gas cartridge 674 and a conductive wire 675.

Figure 22:
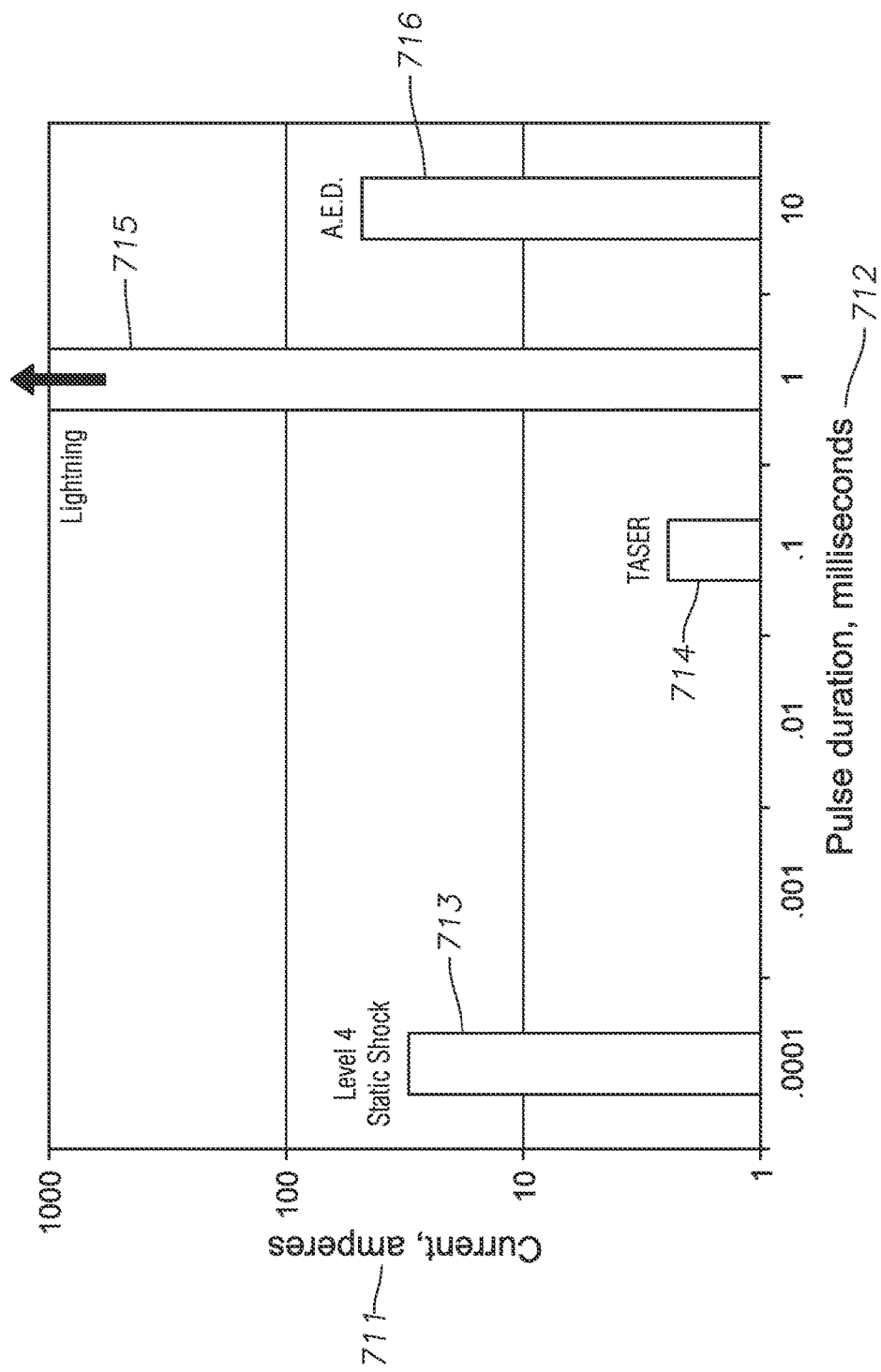
FIG. 22 is a graph of current as a function of pulse duration according to an embodiment of the invention.

As illustrated in FIG. 22, for example, a stun gun can deliver a lower current than an AED. The graph illustrated in FIG. 22 depicts the relationship between current in amperes 711 and pulse duration in milliseconds 712 for level 4 static shock 713, a TASER 714, lightning 715, and an AED 716. As depicted, TASER X26 peak currents are much lower than those of a strong static shock, for example. The defibrillator pulse is 1 million times longer in duration than the static shock. More specifically, an AED can deliver appropriately 40 mC (millicoulombs) into the person at discharge, in contrast. Consequently, an AED can deliver approximately 400 times the charge of a TASER ECD. For example, the charge from a TASER X26 can be about 100 μC (microcoulombs) or about 624,000,000,000,000 electrons. The charge from the main pulse of TASER M26 can be about 85 μC. Due to the high frequency of the M26 waveform, the net charge can be only 32 μC versus the 88 μC of the X26. The ultra-short electrical pulses applied by TASER ECDs can be intended to stimulate A-motor neurons, which are the nerves that control skeletal muscle contraction, without stimulating cardiac muscle. Consequently, a stun gun can be unable to function as a defibrillator when the energies the stun gun utilizes are too low.

A capacitor can be a key component of a defibrillator design that stores electrons. Distinct waveform formulations can use various size capacitors to generate a voltage and current for defibrillation. The size of the capacitor can impact the amount of energy (e.g., measured in joules) needed to produce a voltage and current. For example, smaller capacitors can use fewer joules to pack the necessary voltage and current punch for effective defibrillation when compared to larger capacitors that use more joules to achieve comparable levels. Voltage can describe the force that pushes electrons through a victim. The amount of voltage stored on a capacitor drives the amount of current available for defibrillation. A higher voltage level can mean a greater force and amount of current that can be delivered for defibrillation. Current can describe movement of electrons, measured in amperes, that achieves defibrillation. For biphasic waveforms, distinctive formulations driven by different device components, waveform shape, and duration can produce current. Impedance can describe the resistance of a victim's body to the flow of current, which is measured in ohms. Human impedance levels can range from 25 ohms to 180 ohms. Voltage gradient can reflect the actual intensity of a defibrillation shock in terms of the electric field it generates within the myocardium itself. An accurate measurement of intra-cardiac voltage gradients can require instrumenting the heart with electrodes to capture the data. Duration can describe the period over which a current is delivered to a victim's heart. A goal can be to deliver therapy over an optimal time period to increase the chance of defibrillation. A sinus rhythm can be a desirable heart rhythm. Normal "sinus" rhythm can mean that a victim's heart is beating normally. Fibrillation can mean chaotic electrical activity in which no pumping occurs. Fibrillation that occurs in the ventricle can be called ventricular fibrillation (VF), and a victim can die unless promptly defibrillated with a strong shock. Asystole can mean a "flat line" rhythm with zero or almost zero electrical activity that is not inducible with electrical stimulation and can be very common with excited delirium with or without any emergency communication department (ECD) involvement. Pulseless electrical activity (PEA) can mean that the heart has some moderate rate electrical activity. That is, an EKG machine can identify heart rhythm that should be producing a pulse but is not producing a pulse; the heart's output is insufficient to produce a pulse. Treatments for PEA can include CPR and various drugs.

An ampere (A) can be a unit of measurement of the number of electrons per second flowing along an electrical path. A milliampere (mA) can be 0.001 amperes (or $10^{-3}$ amperes), and a microampere (μA) can be a millionth of an ampere, i.e., 0.000001 amperes (or $10^{-6}$ amperes). A kiloampere (kA) can be 1,000 amperes, and a megampere (MA) can be 1,000,000 amperes. A volt (V) can be a unit of measurement of voltage, i.e., the electrical pressure pushing an electrical current. An ohm (Ω) can be a unit of measurement of resistance to an electrical current. A coulomb (C) can be a unit of measurement that represents the total number of electrons moved over a given period of time. A coulomb is the SI (International System of Units) base unit of electric charge. One coulomb is equal to 6.24150962915265×1018, or approximately 6.24 quintillion, electrons or elementary charges. One coulomb is the amount of electric charge transported by a current of 1 A in 1 second. A joule (J) can be a unit of measurement that represents the SI unit of electrical, mechanical, and thermal energy. A joule can be the unit of electrical energy equal to the work done when a current of 1 A is passed through a resistance of 1Ω for 1 s. Hence, 1 W of power can equal 1 J of energy per second. A joule can be a unit of energy that is approximately equal to 0.2388 calories of heat energy. A watt (W) can be a unit of measurement that is the SI derived unit of power and is equal to delivery of 1 joule of energy per second. A watt can be a small amount of power; a person climbing a flight of stairs can be doing work at a rate of approximately 200 W. Power can be a function of the voltage and the current, and a Watt can equal $1/746$ horsepower. A hertz (Hz) can be a unit of measurement that represents cycles per second of frequency.

In the drawings and specification, there have been disclosed embodiments of systems, protective casings for smartphones, and associated methods of the present invention, and although specific terms are employed, the terms are used in a descriptive sense only and not for purposes of limitation. The embodiments of systems, protective casings for smartphones, and associated methods of the present invention have been described in considerable detail with specific reference to these illustrated embodiments. It will be apparent, however, that various modifications and changes can be made within the spirit and scope of the embodiments of systems, protective casings for smartphones, and associated methods of the present invention as described in the foregoing specification, and such modifications and changes are to be considered equivalents and part of this disclosure.

That claimed is:

1. A system to enhance use of an automated external defibrillator (AED) device before arrival of emergency medical personnel, the system comprising:
   a mobile phone configured to communicate with the Internet thereby to define a smartphone, the smartphone configured to include:
      one or more processors thereby to define smartphone processors,
      one or more input and output units in communication with the smartphone processors and further in communication with one or more communication networks,
      one or more displays in communication with the smartphone processors,
      one or more speakers in communication with the smartphone processors,
      one or more microphones in communication with the smartphone processors, and
      non-transitory memory medium in communication with the smartphone processors and configured to include one or more smartphone modules, each of the smartphone modules including computer-readable instructions stored in the computer-readable medium that when executed by the smartphone processors cause the smartphone processors to perform operations, the one or more smartphone modules including:
         a defibrillation control module to control defibrillation of a victim; and
   a protective casing abuttingly contacting one or more side portions of the smartphone and retaining the smartphone positioned therein, the protective casing configured to include:
      one or more processors thereby to define casing processors,
      one or more input and output units in communication with the casing processors and further in communication with the smartphone processors,
      one or more sensors in communication with the casing processors,
      one or more capacitors in communication with the casing processors,
      two or more extendable electrode pads in communication with the casing processors and configured to transmit a current responsive to activation of the one or more capacitors,
      non-transitory memory medium in communication with the casing processors and configured to include a plurality of casing modules, each of the casing modules including computer-readable instructions stored in the computer-readable medium of the protective casing that when executed by the casing processors cause the casing processors to perform operations, the plurality of casing modules including:
         a check module to determine, by use of the two or more extendable electrode pads and the one or more sensors, whether the victim's heart rhythm requires an electrical shock to reestablish a normal heart rhythm responsive to the defibrillation control module,
         a space module to measure, by use of the one or more sensors, presence and amount of preselected materials relatively near the system thereby to define environmental data responsive to the check module, and
         a shock module to activate the one or more capacitors and generate an electrical current between the two or more extendable electrode pads to deliver an electrical shock to the victim's chest by use of the two or more extendable electrode pads responsive to the check module, the space module, and the defibrillation control module.

2. The system as defined in claim 1, wherein the two or more extendable electrode pads include a layer of nanomaterials on each surface of the two or more extendable electrode pads adapted to be positioned on the victim thereby to define two or more extendable electrode nanocoated pads.

3. The system as defined in claim 1, wherein operations of the check module include measuring, by use of the two or more extendable electrode pads and the one or more sensors, impedance of a victim's body and determining, responsive to a determination that the victim's heart rhythm requires an electrical shock to reestablish a normal heart rhythm, an electrical shock energy level required to reestablish a normal heart rhythm to the victim's heart.

4. The system as defined in claim 1, wherein the preselected materials include one or more of the following: oxygen, carbon monoxide, $H_2S$ emissions, gases, inflammables, and combustibles.

5. The system as defined in claim 1, wherein the protective casing further includes a compartment adapted to house the two or more extendable electrode pads thereby to separate the two or more extendable electrode pads from one or more other components of the protective casing.

6. The system as defined in claim 5, wherein the compartment is a portion of a body of the protective casing, wherein the protective casing further includes a component that has one or more substantially rectangular faces, is connected to the body of the protective casing by one or more connections, and is adapted to substantially enclose the compartment when in a closed position thereby to define a compartment cover, the compartment cover adapted to enclose the two or more extendable electrode pads when in the closed position, and wherein the smartphone and the protective casing are in communication through a Bluetooth connection.

7. The system as defined in claim 1, wherein the smartphone further includes one or more batteries that provide power to charge the one or more capacitors, and wherein the protective casing further includes a direct current (DC) booster configured to amplify the power provided by the one or more batteries of the smartphone.

8. The system as defined in claim 1, wherein the plurality of casing modules further include:

a sync module to generate an electrical current between the two or more extendable electrode pads in a synchronized cardio version;

a pace module to transcutaneously pace the victim by use of the two or more extendable electrode pads; and a self-regulation module to determine when one or more components of the protective casing require replacement thereby to enable the protective casing to self-regulate.

9. The system as defined in claim 1, wherein the one or more smartphone modules further include:

an augmented virtual reality (AVR) module to generate directions to use the system by use of the one or more displays and the one or more speakers;

a rescue module to transmit geographical information systems (GIS) data associated with the system to emergency medical personnel via the one or more communication networks responsive to the defibrillation control module;

a record module to record biometric status of the victim from time of discovery to arrival of the emergency medical personnel thereby to enhance availability of telemedicine;

a note module to transcribe the recorded biometric status of the victim into medical notes for review by the emergency medical personnel responsive to the record module;

an environmental module to transmit geographical positioning system (GPS) data associated with the system and the environmental data to the emergency medical personnel via the one or more communication networks; and an alert module to transmit data to the emergency medical personnel in real time via the one or more communication networks.

10. The system as defined in claim 1, wherein the protective casing is adapted to snap the smartphone into a locked position when the smartphone is positioned in the protective casing, wherein the protective casing includes an inner cavity that has five or more sides, each of the five or more sides adapted to contact abuttingly one or more side portions of the smartphone when the smartphone is in the locked position, and wherein the protective casing is adapted to comply with OSHA standards.

11. The system as defined in claim 1, wherein each of the one or more smartphone modules is associated with one or more applications of the smartphone.

12. A protective casing to enhance use of an automated external defibrillator (AED) device before arrival of emergency medical personnel and adapted to abuttingly contact one or more side portions of and retain a mobile phone configured to communicate with the Internet thereby to define a smartphone when the smartphone is positioned therein, the protective casing comprising:

one or more processors thereby to define casing processors;

one or more input and output units in communication with the casing processors and further in communication with a smartphone;

one or more sensors in communication with the casing processors;

one or more capacitors in communication with the casing processors;

two or more extendable electrode pads in communication with the casing processors and configured to transmit a current responsive to activation of the one or more capacitors; and non-transitory memory medium in communication with the casing processors and configured to include a plurality of modules, each of the modules including computer-readable instructions stored in the computer-readable medium that when executed by the casing processors cause the casing processors to perform operations, the plurality of modules including:

a check module to determine, by use of the two or more extendable electrode pads and the one or more sensors, whether the victim's heart rhythm requires an electrical shock to reestablish a normal heart rhythm responsive to input from the smartphone, a space module to measure, by use of the one or more sensors, presence and amount of preselected materials relatively near the protective casing thereby to define environmental data responsive to the check module, and a shock module to activate the one or more capacitors and generate an electrical current between the two or more extendable electrode pads to deliver an electrical shock to the victim's chest by use of the two or more extendable electrode pads responsive to the check module, the space module, and input from the smartphone.

13. The protective casing as defined in claim 12, wherein the two or more extendable electrode pads include a layer of nanomaterials on each surface of the two or more extendable electrode pads adapted to be positioned on the victim thereby to define two or more extendable electrode nano-coated pads.

14. The protective casing as defined in claim 12, wherein operations of the check module include measuring, by use of the two or more extendable electrode pads and the one or more sensors, impedance of a victim's body and determining, responsive to a determination that the victim's heart rhythm requires an electrical shock to reestablish a normal heart rhythm, an electrical shock energy level required to reestablish a normal heart rhythm to the victim's heart.

15. The protective casing as defined in claim 12, wherein the preselected materials include one or more of the following: oxygen, carbon monoxide, $H_2S$ emissions, gases, inflammables, and combustibles.

16. The protective casing as defined in claim 12, wherein the protective casing further comprises a compartment adapted to house the two or more extendable electrode pads thereby to separate the two or more extendable electrode pads from one or more other components of the protective casing.

17. The protective casing as defined in claim 16, wherein the compartment is a portion of a body of the protective casing, wherein the protective casing further includes a component that has one or more substantially rectangular faces, is connected to the body of the protective casing by one or more connections, and is adapted to substantially enclose the compartment when in a closed position thereby to define a compartment cover, the compartment cover adapted to enclose the two or more extendable electrode pads when in the closed position, and wherein the protective casing is in communication with the smartphone through a Bluetooth connection.

18. The protective casing as defined in claim 12, wherein one or more batteries of the smartphone provide power to charge the one or more capacitors, and wherein the protective casing further includes a direct current (DC) booster configured to amplify the power provided by the one or more batteries of the smartphone.

19. The protective casing as defined in claim 12, wherein the plurality of casing modules further include:
- a sync module to generate an electrical current between the two or more extendable electrode pads in a synchronized cardio version;
- a pace module to transcutaneously pace the victim by use of the two or more extendable electrode pads; and
- a self-regulation module to determine when one or more components of the protective casing require replacement thereby to enable the protective casing to self-regulate.

20. The protective casing as defined in claim 12, wherein the protective casing is adapted to snap the smartphone into a locked position when the smartphone is positioned in the protective casing, wherein the protective casing includes an inner cavity that has five or more sides, each of the five or more sides adapted to contact abuttingly one or more side portions of the smartphone when the smartphone is in the locked position, and wherein the protective casing is adapted to comply with OSHA standards.

21. A method to assemble a system to enhance use of an automated external defibrillator (AED) device before arrival of emergency medical personnel, the method comprising positioning a mobile phone configured to communicate with the Internet thereby to define a smartphone in a protective casing adapted to abuttingly contact one or more side portions of the smartphone and retain the smartphone, the protective casing configured to include one or more sensors, one or more capacitors, and two or more extendable electrode pads configured to transmit a current responsive to activation of the one or more capacitors.

22. A method to use a protective casing for a mobile phone configured to communicate with the Internet thereby to define a smartphone to enhance use of an automated external defibrillator (AED) device before arrival of emergency medical personnel, the protective casing positioned to abuttingly contact one or more side portions of a smartphone and retain the smartphone, the protective casing configured to include one or more sensors, one or more capacitors, and two or more extendable electrode pads configured to transmit a current responsive to activation of the one or more capacitors, the method comprising:
- positioning the two or more extendable electrode pads on a victim's chest;
- determining, by use of the two or more extendable electrode pads and the one or more sensors, whether the victim's heart rhythm requires an electrical shock to reestablish a normal heart rhythm responsive to input from the smartphone;
- measuring, by use of the one or more sensors, presence and amount of preselected materials relatively near the protective casing thereby to define environmental data responsive to determination of whether the victim's heart rhythm requires an electrical shock to reestablish a normal heart rhythm;
- activating the one or more capacitors responsive to measurement of presence and amount of the preselected materials relatively near the protective casing; and
- generating an electrical current between the two or more extendable electrode pads to deliver an electrical shock to the victim's chest by use of the two or more extendable electrode pads responsive to activation of the one or more capacitors.

\* \* \* \* \*